(12) United States Patent
Boles et al.

(10) Patent No.: US 8,063,194 B2
(45) Date of Patent: Nov. 22, 2011

(54) **SPECIFIC ARABINOSE TRANSPORTER FROM THE YEAST *PICHIA STIPITIS*, AND USES THEREOF**

(75) Inventors: Eckhard Boles, Darmstadt (DE); Marco Keller, Boruleiw (DE)

(73) Assignee: Johann Wolfgang Goethe-Universität Frankfurt Am Main, Frankfurt am Main (DE)

( * ) Notice: Subject to any disclaimer, the term of this patent is extended or adjusted under 35 U.S.C. 154(b) by 0 days.

(21) Appl. No.: 12/520,487

(22) PCT Filed: Dec. 7, 2007

(86) PCT No.: PCT/EP2007/010668
§ 371 (c)(1),
(2), (4) Date: Jan. 27, 2010

(87) PCT Pub. No.: WO2008/080505
PCT Pub. Date: Jul. 10, 2008

(65) Prior Publication Data
US 2010/0143936 A1   Jun. 10, 2010

(30) Foreign Application Priority Data
Dec. 20, 2006 (DE) .......................... 10 2006 060 381

(51) Int. Cl.
*C07H 21/02* (2006.01)
(52) U.S. Cl. ..................... 536/23.7; 536/23.1; 435/69.1; 435/69.9; 435/69.2; 435/254.2; 435/254.21
(58) Field of Classification Search .......................... None
See application file for complete search history.

(56) References Cited

FOREIGN PATENT DOCUMENTS
WO   WO 2007/143245   12/2007
WO   WO 2007/143247   12/2007

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Fonseca et al., "L-Arabinose transport and catabolism in yeast", *FEBS Journal*, 2007, vol. 274, pp. 3589-3600.
Jeffries et al., "Genome sequence of the lignocellulose-biconverting and xylose-fermenting yeast *Pichia stipitis*", *Nature Biotechnology*, 2007, vol. 25, No. 3, pp. 319-326.
Jeffries et al., "Metabolic engineering for improved fermentation of pentoses by yeasts", *Applied Microbiology and Biotechnology*, 2004, vol. 63, pp. 495-509.
Richard et al., "Production of ethanol from L-arabinose by *Saccharomyces cerevisiae* containing a fungal L-arabinose pathway", *FEMS Yeast Reasearch*, 2003, vol. 3, pp. 185-189.

* cited by examiner

*Primary Examiner* — Jennifer Graser
(74) *Attorney, Agent, or Firm* — Saliwanchik, Lloyd & Eisenschenk

(57) ABSTRACT

The present invention relates to a polypeptide which has a novel specific arabinose transporter function as well as to nucleic acids coding therefore. The invention further relates to host cells, in particular modified yeast strains which contain the coding nucleic acids and express the polypeptide and functionally integrate it into the plasma membrane and are thus able to absorb L-arabinose. When using modified host cells which express additional proteins of the arabinose metabolic pathway, arabinose can be fermented by these cells, in particular into ethanol. The present invention is therefore relevant, inter alia, in connection with the production of biochemicals from biomass, such as bioethanol for example.

12 Claims, 15 Drawing Sheets

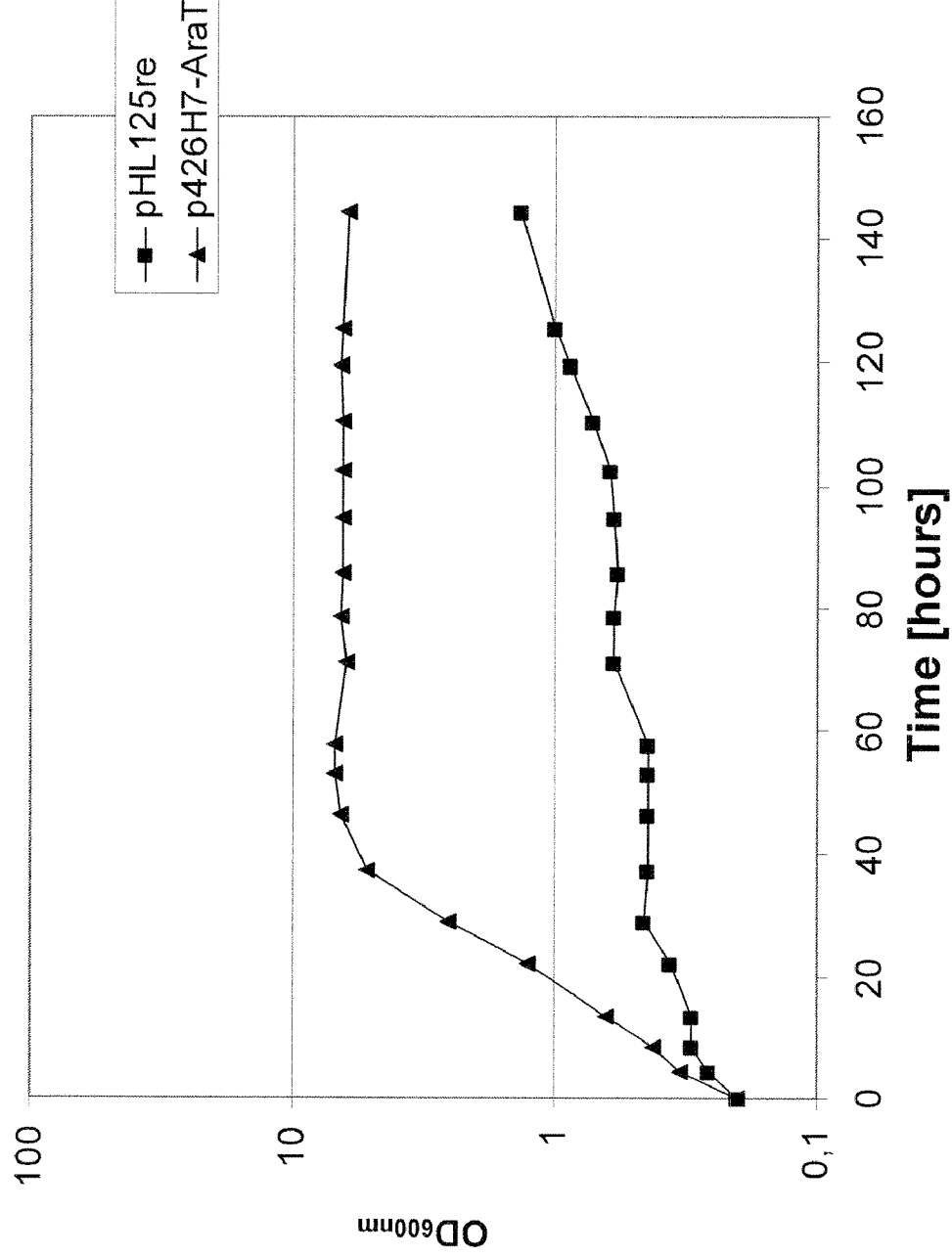

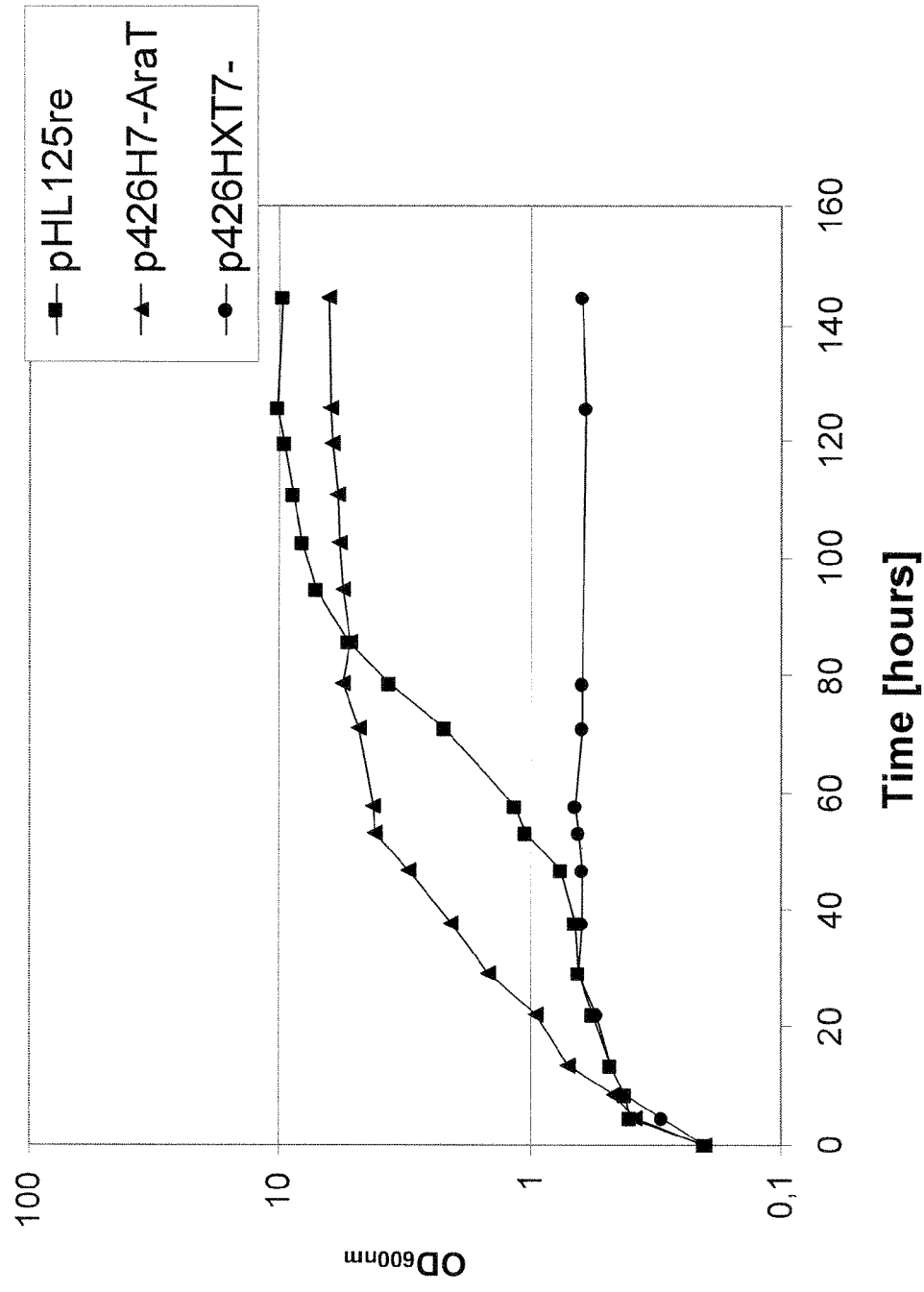

SEQUENCE LISTING

<160> NUMBER OF SEQ ID NOS: 4

<210> SEQ ID NO 1
<211> LENGTH: 542
<212> TYPE: PRT
<213> ORGANISM: Pichia stipitis

<400> SEQUENCE: 1

```
Met Ser Tyr Glu Asp Lys Leu Val Gln Pro Ala Leu Lys Phe Arg Thr
1               5                   10                  15

Phe Leu Asp Arg Leu Pro Asn Ile Tyr Asn Val Tyr Ile Ile Ala Ser
            20                  25                  30

Ile Ser Cys Ile Ser Gly Met Met Phe Gly Phe Asp Ile Ser Ser Met
        35                  40                  45

Ser Ala Phe Ile Gly Glu Asp Asp Tyr Lys Asn Phe Asn Asn Pro
    50                  55                  60

Gly Ser Asp Ile Gln Gly Phe Ile Thr Ser Cys Met Ala Leu Gly Ser
65                  70                  75                  80

Phe Phe Gly Ser Ile Val Ser Ser Phe Ile Ser Glu Pro Phe Gly Arg
                85                  90                  95

Arg Ala Ser Leu Leu Leu Cys Ser Phe Phe Trp Met Val Gly Ala Ala
            100                 105                 110

Val Gln Ser Ser Ser Gln Asn Arg Ala Gln Leu Met Ile Gly Arg Ile
        115                 120                 125

Ile Ala Gly Phe Gly Val Gly Phe Gly Ser Ser Val Ala Pro Val Tyr
    130                 135                 140

Gly Ser Glu Leu Ala Pro Arg Lys Ile Arg Gly Phe Val Gly Gly Ile
145                 150                 155                 160

Phe Gln Phe Cys Val Thr Leu Gly Ile Leu Ile Met Phe Tyr Ile Cys
                165                 170                 175

Tyr Gly Leu His Phe Ile Asn Gly Val Gly Ser Phe Arg Ile Ala Trp
            180                 185                 190

Gly Leu Gln Ile Val Pro Gly Leu Val Leu Phe Val Gly Cys Phe Phe
        195                 200                 205

Ile Pro Glu Ser Pro Arg Trp Leu Ala Lys His Gly Tyr Trp Asp Glu
    210                 215                 220

Ala Glu Phe Ile Val Ala Gln Ile Gln Ala Lys Gly Asn Arg Glu Asp
225                 230                 235                 240

Pro Asp Val Leu Ile Glu Ile Ser Glu Ile Lys Asp Gln Ile Leu Ile
                245                 250                 255

Glu Glu Asn Leu Lys Ser Phe Gly Tyr Val Asp Leu Phe Thr Lys Lys
            260                 265                 270

Tyr Ile Arg Arg Thr Leu Thr Ala Ile Phe Ala Gln Ile Trp Gln Gln
        275                 280                 285

Leu Thr Gly Met Asn Val Met Met Tyr Tyr Ile Val Tyr Ile Phe Asn
    290                 295                 300

Met Ala Gly Tyr Ser Asn Asn Ala Asn Leu Val Ala Ser Ser Ile Gln
305                 310                 315                 320

Tyr Val Leu Asn Thr Ala Ala Thr Val Pro Ala Leu Phe Leu Met Asp
                325                 330                 335

Tyr Ile Gly Arg Arg Arg Leu Leu Ile Gly Gly Ala Ile Met Met Met
            340                 345                 350

Ile Phe Gln Phe Gly Val Ala Gly Ile Leu Gly Lys Tyr Ser Val Pro
        355                 360                 365
```

```
Val Pro Gly Gly Leu Pro Gly Asn Pro Thr Val Thr Ile Gln Ile Pro
        370             375             380

Glu Asp Asn Lys Ser Ala Ala Arg Gly Val Ile Ala Cys Cys Tyr Leu
385             390             395                 400

Phe Val Val Ser Phe Ala Leu Ser Trp Gly Val Gly Ile Trp Val Tyr
                405             410             415

Cys Ser Glu Val Trp Gly Asp Ser Ala Ser Arg Gln Arg Gly Ala Ala
            420             425             430

Val Ser Thr Ala Ala Asn Trp Ile Leu Asn Phe Ala Ile Ala Met Tyr
        435             440             445

Thr Pro Ser Ser Phe Lys Asn Ile Thr Trp Lys Thr Tyr Ile Ile Tyr
    450             455             460

Ala Val Phe Cys Leu Val Met Ala Ile His Val Tyr Phe Gly Phe Pro
465             470             475                 480

Glu Thr Lys Gly Lys Arg Leu Glu Glu Val Gly Gln Met Trp Asp Glu
                485             490             495

Asn Val Pro Ala Trp Arg Ser Ser Trp Gln Pro Thr Val Pro Leu
            500             505             510

Leu Ser Asp Ala Asp Leu Ala His Lys Met Asp Val Ser His Lys Glu
        515             520             525

Glu Gln Ser Pro Asp Ala Glu Ser Ser Ser Glu Glu Lys Pro
    530             535             540

<210> SEQ ID NO 2
<211> LENGTH: 1629
<212> TYPE: DNA
<213> ORGANISM: Pichia stipitis

<400> SEQUENCE: 2
atgagctacg aagataaact cgttcaacct gccttgaagt caggacctt cttggacaga      60 cttccaaaca tttacaatgt gtacattatt gcatctattt cctgtatttc aggtatgatg    120
ttcggttttg atatttcatc tatgtctgct tttataggtg aagatgacta caagaacttt    180
ttcaataatc caggctcaga catccaaggt tttatcactt cctgtatggc tttaggttct    240
ttcttcggtt ccatagtctc ttccttcatt tccgaaccat ttggtagaag agcatccttg    300
ttgttgtgtt cattcttctg gatggtcggt gctgctgtac aatcatcttc tcaaaacaga    360
gcccaattga tgatcggacg tatcatcgct ggtttcggtg ttggttttgg ttcttctgtt    420
gctccagttt acggttccga attggctcca agaaagatta gaggttttgt tggtggtatt    480
ttccaattct gtgttacctt gggtatcttg attatgttct acatttgtta cggtttgcat    540
ttcattaacg tgttggctc tttcagaatt gcttggggtt tacaaattgt cccaggtttg    600
gttttatttg tcggttgttt ctttattcca gaatctccaa gatggttagc caaacatggt    660
tactgggatg aagcagaatt catcgttgcc caaattcaag ctaagggtaa tagagaagac    720
ccagacgtgt tgattgaaat ctccgaaatc aaggaccaaa ttttgattga agaaaacctc    780
aagagtttcg gttacgtcga cttattcacc aagaagtata tcagaagaac tttaactgcc    840
atatttgctc aaatctggca acaattgacc ggtatgaatg ttatgatgta ctatattgtc    900
tacattttca acatggccgg ttactctaac aacgcaaact tggttgcctc ttccatccaa    960
tacgtcttga cactgctgc aactgttcca gctttgtttt taatggatta cattggcaga   1020
agaagattgt tgattggagg tgccatcatg atgatgattt tccaatttgg tgttgctggt   1080
atcttaggta aatactccgt ccccgttcca ggcggtcttc aggtaaaccc aactgttacc   1140
atccaaatcc cagaagacaa caagtcagct gctagaggtg ttattgcttg ttgttactta   1200
```

```
ttcgttgtat cattcgctct gagttggggt gtcggtatct gggtctactg ttcagaagtt    1260
tggggtgact ctgcttccag acagagaggt gctgctgttt caactgctgc caactggatt    1320
cttaactttg ctattgccat gtacactcca tcttccttca agaatatcac ctggaagact    1380
tacatcatct acgccgtctt ctgtcttgtt atggcaatcc atgtctactt tggattccca    1440
gaaaccaagg gcaagcgttt ggaagaagtc ggacaaatgt gggacgaaaa tgttcccgca    1500
tggagatctt ccagctggca accaactgtt ccattgttgt cagatgccga cttggcacac    1560
aagatggatg tttcccacaa ggaagagcaa tctccagatg ccgagtcaag ttctgaggaa    1620
aagccttaa                                                            1629

<210> SEQ ID NO 3
<211> LENGTH: 1629
<212> TYPE: DNA
<213> ORGANISM: Pichia stipitis

<400> SEQUENCE: 3
atgtcttacg aagacaagtt ggttcaacca gctttgaagt tcagaacctt cttggacaga      60
ttgccaaaca tttacaacgt ttacattatt gcttctatt cttgtatttc tggtatgatg    120
ttcggtttcg acatttcttc tatgtctgct ttcattggtg aagacgacta caagaacttc    180
ttcaacaacc caggttctga cattcaaggt ttcattacct cttgtatggc tttgggttct    240
ttcttcggtt ctattgtttc ttctttcatt tctgaaccat cggtagaag agcttctttg    300 ttgttgtgtt ctttcttctg gatggttggt gctgctgttc aatcttcttc tcaaaacaga    360
gctcaattga tgattggtag aattattgct ggtttcggtg ttggtttcgg ttcttctgtt    420
gctccagttt acggttctga attggctcca agaaagatta gaggtttcgt tggtggtatt    480
ttccaattct gtgttacctt gggtattttg attatgttct acatttgtta cggtttgcac    540
ttcattaacg tgttggttc tttcagaatt gcttggggtt tgcaaattgt tccaggtttg    600
gttttgttcg ttggttgttt cttcattcca gaatctccaa gatggttggc taagcacggt    660
tactgggacg aagctgaatt cattgttgct caaattcaag ctaagggtaa cagagaagac    720
ccagacgttt tgattgaaat ttctgaaatt aaggaccaaa ttttgattga agaaaacttg    780
aagtctttcg gttacgttga cttgttcacc aagaagtaca ttagaagaac cttgaccgct    840
attttcgctc aaatttggca acaattgacc ggtatgaacg ttatgatgta ctacattgtt    900
tacattttca acatggctgg ttactctaac aacgctaact tggttgcttc ttctattcaa    960
tacgttttga caccgctgc taccgttcca gctttgttct tgatgactaa cattggtaga   1020
agaagattgt tgattggtgg tgctattatg atgatgattt tccaattcgg tgttgctggt   1080
attttgggta gtactctgt tccagttcca ggtggtttgc aggtaaccc aaccgttacc   1140 attcaaattc cagaagacaa caagtctgct gctagaggtg ttattgcttg ttgttacttg   1200
ttcgttgttt ctttcgcttt gtcttggggt gttggtattt gggttactg ttctgaagtt   1260 tggggtgact ctgcttctag acaaagaggt gctgctgttt ctaccgctgc taactggatt   1320
ttgaacttcg ctattgctat gtacaccca tcttctttca agaacattac ctggaagacc   1380
tacattattt acgctgtttt ctgtttggtt atggctattc acgtttactt cggtttccca   1440
gaaaccaagg gtaagagatt ggaagaagtt ggtcaaatgt gggacgaaaa cgttccagct   1500
tggagatctt cttcttggca accaaccgtt ccattgttgt ctgacgctga cttggctcac   1560
aagatggacg tttctcacaa ggaagaacaa tctccagacg ctgaatcttc ttctgaagaa   1620
aagccataa                                                           1629
```

<210> SEQ ID NO 4
<211> LENGTH: 2430
<212> TYPE: DNA
<213> ORGANISM: Pichia stipitis

<400> SEQUENCE: 4

```
acaattttgt ggaataatcc cccaccttga taatccttct taggaacaat aaccggcgag      60
atgtgcgggg cacgtcagga aacttaacct tgtcgcccta aattgccgtg aaggagagcc     120
atacgatgga actccaaact tttatagtac atatagagtg gagtttgttt ggggaagtgg     180
gaccatgggt caggaatttt gccgaaaaag ggcggttttg ttcactccta gtgcataatg     240
cctgtgtata gacgatcaac ttgtattaat gtctgcatac cccaaatatt cacaattgac     300
ccgcatcaaa aaataattct atctgacatc acgtatgcaa atacagtgag gaaatccatt     360
cttgctgcca actcttcgcc tttttactca tccttgaaga aggaatcttt gcaatataaa     420
agtaagatga aattcctctt atttacaat gttttgtcaa gtctttaaga aatttactct     480
atcgtattta atattatatc atgagctacg aagataaact cgttcaacct gccttgaagt     540
tcaggacctt cttggacaga cttccaaaca tttacaatgt gtacattatt gcatctattt     600
cctgtatttc aggtatgatg ttcggttttg atatttcatc tatgtctgct tttataggtg     660
aagatgacta caagaacttt ttcaataatc caggctcaga catccaaggt tttatcactt     720
cctgtatggc tttaggttct ttcttcggtt ccatagtctc ttccttcatt tccgaaccat     780
ttggtagaag agcatccttg ttgttgtgtt cattcttctg gatggtcggt gctgctgtac     840
aatcatcttc tcaaaacaga gcccaattga tgatcggacg tatcatcgct ggtttcggtg     900
ttggttttgg ttcttctgtt gctccagttt acggttccga attggctcca agaaagatta     960
gaggttttgt tggtggtatt ttccaattct gtgttacctt gggtatcttg attatgttct    1020
acatttgtta cggtttgcat ttcattaacg gtgttggctc tttcagaatt gcttggggtt    1080
tacaaattgt cccaggtttg gtttatttg tcggttgttt ctttattcca gaatctccaa    1140
gatggttagc caaacatggt tactgggatg aagcagaatt catcgttgcc caaattcaag    1200
ctaagggtaa tagagaagac ccagacgtgt tgattgaaat ctccgaaatc aaggaccaaa    1260
ttttgattga agaaaacctc aagagtttcg gttacgtcga cttattcacc aagaagtata    1320
tcagaagaac tttaactgcc atatttgctc aaatctggca acaattgacc ggtatgaatg    1380
ttatgatgta ctatattgtc tacattttca acatggccgg ttactctaac aacgcaaact    1440
tggttgcctc ttccatccaa tacgtcttga acactgctgc aactgttcca gctttgtttt    1500
taatggatta cattggcaga agaagattgt tgattggagg tgccatcatg atgatgattt    1560
tccaatttgg tgttgctggt atcttaggta aatactccgt ccccgttcca ggcggtcttc    1620
caggtaaccc aactgttacc atccaaatcc cagaagacaa caagtcagct gctagaggtg    1680
ttattgcttg ttgttactta ttcgttgtat cattcgctct gagttggggt gtcggtatct    1740
gggtctactg ttcagaagtt tggggtgact ctgcttccag acagagaggt gctgctgttt    1800
caactgctgc caactggatt cttaactttg ctattgccat gtacactcca tcttccttca    1860
agaatatcac ctggaagact tacatcatct acgccgtctt ctgtcttgtt atggcaatcc    1920
atgtctactt tggattccca gaaaccaagg gcaagcgttt ggaagaagtc ggacaaatgt    1980
gggacgaaaa tgttcccgca tggagatctt ccagctggca accaactgtt ccattgttgt    2040
cagatgccga cttggcacac aagatggatg tttcccacaa ggaagagcaa tctccagatg    2100
ccgagtcaag ttctgaggaa aagccttaaa ctaaattgat atgaataaac ctgttgcaac    2160
agttgtgtga agtcaattgt tcacgtctta caataatgtc tttatgaaat gctttaaaca    2220
```

-continued

```
atgtgctata ttaatttatc tgtttactat cttctgtagt acttcatata catccattat    2280
cgaagatact cttcgtagac caatacccta atctcgcctg tacttcactg attgctgctc    2340
tgctttaggt cccttcgaca cttacttttt gttctcgaat atatgacttg ttcatcgccc    2400
taccaccaac tgaatcattg gtccgctatt                                     2430
```

SPECIFIC ARABINOSE TRANSPORTER FROM THE YEAST *PICHIA STIPITIS*, AND USES THEREOF

This application is a National Stage Application of International Application Number PCT/EP2007/010668, filed Dec. 7, 2007; which claims priority to German Application No. 10 2006 060 381.8, filed Dec. 20, 2006, which are incorporated herein by reference in their entirety.

BACKGROUND OF THE INVENTION

The beer, wine and baking yeast *Saccharomyces cerevisiae* has already been used for centuries for the production of bread, wine and beer owing to its characteristic of fermenting sugar to ethanol and carbon dioxide. In biotechnology, *S. cerevisiae* is used particularly in ethanol production for industrial purposes, in addition to the production of heterologous proteins. Ethanol is used in numerous branches of industry as an initial substrate for syntheses. Ethanol is gaining increasing importance as an alternative fuel, due to the increasingly scarce presence of oil, the rising oil prices and continuously increasing need for petrol worldwide.

In order to make possible a favourably-priced and efficient bioethanol production, the use of lignocellulose-containing biomass, such as for example straw, waste from the timber industry and agriculture and the organic component of everyday household waste, presents itself as an initial substrate. Firstly, said biomass is very convenient and secondly is present in large quantities. The three major components of lignocellulose are lignin, cellulose and hemicellulose. Hemicellulose, which is the second most frequently occurring polymer after cellulose, is a highly branched heteropolymer. It consists of pentoses (L-arabinose, D-xylose), uronic acids (4-O-methyl-D-glucuronic acid, D-galacturonic acid) and hexoses (D-mannose, D-galactose, L-rhamnose, D-glucose) (see FIG. 1). Although, hemicellulose can be hydrolized more easily than cellulose, but it contains the pentoses L-arabinose and D-xylose, which can normally not be converted by the yeast *S. cerevisae*.

In order to be able to use pentoses for fermentations, these must firstly enter the cell through the plasma membrane. Although *S. cerevisiae* is not able to metabolize D-xylose, it can uptake D-xylose into the cell. However, *S. cerevisiae* does not have a specific transporter. The transport takes place by means of the numerous hexosetransporters. The affinity of the transporters to D-xylose is, however, distinctly lower than to D-glucose (Kotter and Ciriacy, 1993). In yeasts which are able to metabolize D-xylose, such as for example *P. stipitis, C. shehatae* or *P. tannophilus* (Du Preez et al., 1986), there are both unspecific low-affinity transporters, which transport D-glucose, and also specific high-affinity proton symporters only for D-xylose (Hahn-Hagerdal et al., 2001).

In earlier experiments, some yeasts were found, such as for example *Candida tropicalis, Pachysolen tannophilus, Pichia stipitis, Candida shehatae*, which by nature ferment L-arabinose or can at least assimilate it. However, these yeast lack entirely the capability of fermenting L-arabinose to ethanol, or they only have a very low ethanol yield (Dien et al., 1996). Moreover, very little is yet known about the uptake of L-arabinose. In the yeast *C. shehatae* one assumes a proton symport (Lucas and Uden, 1986). In *S. cerevisiae*, it is known from the galactose permease Gal2 that it also transports L-arabinose, which is very similar in structure to D-galactose. (Kou et al., 1970).

Alcoholic fermentation of pentoses in biotechnologically modified yeast strains of *S. cerevisiae*, wherein inter alia various genes of the yeast strain *Pichia stipitis* were used for the genetic modification of *S. cerevisiae*, was described in recent years particularly in connection with the fermentation of xylose. The engineering concentrated here particularly on the introduction of the genes for the initial xylose assimilation from *Pichia stipitis*, a xylose-fermenting yeast, into *S. cerevisiae*, i.e. into a yeast which is traditionally used in the ethanol production from hexose (Jin et al. 2004).

Jeppson et al. (2006) describe xylose fermentation by *S. cerevisiae* by means of the introduction of a xylose metabolic pathway which is either similar to that in the yeasts *Pichia stipitis* and *Candida shehatae*, which naturally use xylose, or is similar to the bacterial metabolic pathway.

Katahira et al. (2006) describe sulphuric acid hydrolysates of lignocellulose biomass such as wood chips, as an important material for the production of fuel bioethanol. In this study, a recombinant yeast strain was constructed, which is able to ferment xylose and cellooligosaccharides. For this, various genes were integrated into this yeast strain and namely for the inter-cellular expression of xylose reductase and xylitol dehydrogenase from *Pichia stipitis* and xylulokinase from *S. cerevisiae* and for the presentation of beta-glucosidase from *Aspergillus acleatus* on the cell surface. In the fermentation of sulphuric acid hydrolysates of wood chips, xylose and cellooligosaccharides were fully fermented by the recombinant strain after 36 hours.

Pitkanen et al. (2005) describe the obtaining and characterizing of xylose chemostat isolates of a *S. cervisiae* strain, which over-expresses genes of *Pichia stipitis* coding for xylose reductase and xylitol dehydrogenase and the gene which codes endogenous xylulokinase. The isolates were obtained from aerobic chemostat cultures on xylose as the single or major carbon source. Under aerobic conditions on minimal medium with 30 g/l xylose, the growth rate of the chemostat isolates was 3 times higher than that of the original strain (0.15 $h^{-1}$ compared with 0.05 $h^{-1}$). The xylose uptake rate was increased almost two-fold. The activities of the key enzymes of the pentose phosphate metabolic pathway (transketolase, transaldolase) were increased two-fold, whilst the concentrations of their substrates (pentose-5-phosphates, sedoheptulose-7-phosphate) were lowered accordingly.

Becker and Boles (2003) describe the engineering and the selection of a laboratory strain of *S. cerevisiae* which is able to use L-arabinose for growth and for fermenting it to ethanol. This was possible due to the over-expression of a bacterial L-arabinose metabolic pathway, consisting of *Bacillus subtilis* AraA and *Escherichia coli* AraB and AraD and simultaneous over-expression of yeast galactose permease transporting L-arabinose in the yeast strain. Molecular analysis of the selected strain showed that the predetermining precondition for a use of L-arabinose is a lower activity of L-ribulokinase. However, inter alia, a very slow growth is reported from this yeast strain (see FIG. 2).

Therefore, a need exists in the art for specific pentose transporters, in particular L-arabinose transporters, which allow to specifically take up pentoses, in particular L-arabinose, into cells, such as yeast cells, and therefore to promote a utilization and fermentation of pentoses, in particular L-arabinose.

It is therefore an object of the present invention to provide specific pentose transporters, such as arabinose transporters.

The problem is solved according to the invention by providing polypeptides which have an in vitro and/or in vivo pentose transport function, and variants and fragments thereof.

In particular, the polypeptide according to the invention is selected from the group of a. a polypeptide, which is at least 70%, preferably at least 80% identical to the amino acid sequence according to SEQ ID NO:1 and has an in vitro and/or in vivo pentose transport function,
b. a naturally occurring variant of a polypeptide comprising the amino acid sequence according to SEQ ID NO:1, which has an in vitro and/or in vivo pentose transport function,
c. a polypeptide which is identical to the amino acid sequence according to SEQ ID NO:1 and has an in vitro and/or in vivo pentose transport function, and
d. a fragment of the polypeptide of a., b, or c., comprising a fragment of at least 100 continuous amino acids according to SEQ ID NO:1.

Preferably, the polypeptide according to the invention comprises a fragment of at least 200 or 300 continuous amino acids according to SEQ ID NO:1. Here, such a fragment is characterized in that it has an in vitro and/or in vivo pentose transport function.

In a preferred embodiment, a polypeptide according to the invention comprises a fragment of 502 amino acids which corresponds to the first 502 amino acids of SEQ ID NO:1. Such a fragment is characterized in that it has an in vitro and/or in vivo pentose transport function.

The polypeptide according to the invention preferably comprises a polypeptide which is at least 90%, preferably 95%, more preferably 99% identical to the amino acid sequence according to SEQ ID NO:1 and has an in vitro and/or in vivo pentose transport function.

Variants of the polypeptides according to the invention can also be those which have conservative amino acid substitutions or smaller deletions and/or insertions as long as these modifications do not substantially affect the in vitro and/or in vivo pentose transport function.

Polypeptides according to the invention can further comprise heterologous amino acid sequences. The skilled artisan can select suitable heterologous amino acid sequences depending on the application or use.

Preferably, the pentose is arabinose, in particular L-arabinose, so that a polypeptide according to the invention preferably has an in vitro and/or in vivo arabinose transport function, in particular an L-arabinose transport function.

The polypeptide according to the invention preferably originates from a yeast, preferably from *Pichia*, in particular *Pichia stipitis*.

The problem is further solved according to the invention by providing isolated nucleic acid molecules which code for a polypeptide according to the invention.

Preferably, a nucleic acid molecule according to the invention is at least 90%, preferably 95% and more preferably 99% identical to the nucleic acid sequence according to SEQ ID NO:2 or 3.

A nucleic acid molecule according to the invention further comprises vector nucleic acid sequences, preferably expression vector sequences. Vector nucleic acid sequences are preferably selected from sequences which are comprised from the vectors of the group consisting of YEp24, p426HXT7-6HIS, p426Met25, pYES260, pYES263, pVTU260, pVTU263, pVTL260, pVTL263. For further embodiments, see FIGS. 6A-E and Example 3.

Nucleic acid molecules according to the invention can furthermore comprise nucleic acid sequences which code for further heterologous polypeptides. The skilled artisan can select suitable nucleic acid sequences which code for the further heterologous polypeptides himself, depending on the application or use. These include for example antibiotic resistance marker sequences.

Nucleic acid molecules according to the invention preferably comprise dsDNA, ssDNA, PNA, CNA, RNA or mRNA or combinations thereof.

The problem is further solved according to the invention by providing host cells which contain at least one nucleic acid molecule according to the invention. Host cells according to the invention preferably also express said at least one nucleic acid molecule according to the invention.

A host cell according to the invention is, in particular, a fungal cell and preferably a yeast cell, such as *Saccharomyces* species, e.g. *S. cerevisiae, Kluyveromyces* sp., e.g. *K. lactis, Hansenula* sp., e.g. *H. polymorpha, Pichia* sp., e.g. *P. pastoris, Yarrowia* sp., e.g. *Y. lipolytica*.

Preferably, host cells according to the invention further contain nucleic acid molecules which code for proteins of the arabinose metabolic pathway, in particular for L-ribulokinase, L-ribulose-5-P 4-epimerase, L-arabinose-isomerase.

Preferably, these concern proteins of the bacterial arabinose metabolic pathway, in particular *E. coli* araB L-ribulokinase, *E. coli* araB L-ribulose-5-P 4-epimerase and *B. subtilis* araA L-arabinose-isomerase. See also FIGS. 2 and 3.

Particularly preferred host cells of this invention are cells of the strain MKY06-4P, which was deposited, under the terms of the Budapest Treaty, on 23 Aug. 2006 at the German Collection of Microorganisms and Cell Cultures, located at Inhoffenstraße 7 B, 38124 Braunschweig, Germany, under accession number DSM 18544. See also FIG. 3.

Further, the subject MKY06-4P deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which ma issue disclosing the culture. The depositor acknowledges the duty to replace the deposit should the depository be unable to furnish a sample when requested, due to the condition of the deposit. During pendency of this application, access to the deposit will be afforded to one determined by the Commissioner to be entitled thereto. All restrictions on the availability to the public of the subject culture deposit will be irrevocably removed upon the granting of a patent disclosing it.

A preferred host cell according to this invention is a yeast cell which was modified by the introduction and expression of the genes araA (L-arabinose-isomerase), araB (L-ribulokinase) and araD (L-ribulose-5-P-4-epimerase) and in addition over-expresses a TAL1 (transaldolase) gene, as described for example by the inventors in EP 1 499 708 B1, and in addition to this contains at least one nucleic acid molecule according to the invention.

The problem is further solved according to the invention by providing antibodies or antibody fragments, comprising an immunologically active part, which binds selectively to a polypeptide according to the invention. Methods for the generation of antibodies or antibody fragments are known in the art.

The problem is further solved according to the invention by methods for the production of a polypeptide according to the invention. Such a method comprises the cultivating of a host cell according to the invention under conditions by which a nucleic acid molecule according to the invention is expressed. General methods for the generation of polypeptides by means of cell culture are known in the art.

The problem is further solved according to the invention by a kit comprising a compound which selectively binds to a polypeptide according to the invention, if applicable with further additives and instructions for use.

The compound is preferably a pentose, such as for example arabinose, and in particular L-arabinose, or a derivative of such a pentose.

The problem is further solved according to the invention by methods for identifying a compound which binds to a polypeptide according to the invention and/or modulates its activity. Such a method comprises the following steps:

Contacting a polypeptide or a cell, which expresses a polypeptide according to the invention, with a test compound, and Determining whether the polypeptide binds to the test compound and, if applicable Determining whether the test compound modulates the activity of the polypeptide.

The compound is preferably a pentose, such as for example arabinose, and in particular L-arabinose, or a derivative of such a pentose.

The problem is further solved according to the invention by methods for modulating the activity of a polypeptide according to the invention. Such a method comprises contacting a polypeptide or a cell, which expresses a polypeptide according to the invention, with a compound which binds to the polypeptide in a concentration which is sufficient to modulate the activity of the polypeptide.

The compound is preferably a pentose, such as for example arabinose, and in particular L-arabinose, or a derivative of such a pentose.

The problem is further solved according to the invention by methods for the production of bioethanol. Such a method according to the invention comprises the expression of a nucleic acid molecule according to the invention in a host cell according to the invention.

The polypeptides, nucleic acid molecules and host cells according to the invention are particularly preferably used for the production of bioethanol. For preferred embodiments, reference is made to FIG. 8 and Example 4.

The polypeptides, nucleic acid molecules and host cells according to the invention are further particularly preferably used for the recombinant fermentation of pentose-containing biomaterial.

Specific genes of *Pichia stipitis*, which specifically increase the uptake of the pentose L-arabinose in *S. cerevisiae*, were isolated using a gene bank and integrated into the yeast strain MKY06-3P, which is then able to ferment the L-arabinose to ethanol. The screening of the relevant genes led to a novel specific L-arabinose transporter, the nucleotide- and protein sequence of which is available (see SEQ ID NOs: 1-4). For this, reference is also made to the examples and figures.

Due to the specificity of this novel transporter, after expression in existing ethanol-producing systems the uptake rate for L-arabinose can be improved, because on the one hand the competitive situation with respect to glucose is improved at high L-arabinose concentrations, and on the other hand the transport of L-arabinose becomes more efficient at low L-arabinose concentrations due to a high affinity.

Uptake of L-arabinose

In order that the pentose L-arabinose can be metabolized by *S. cerevisiae*, it must firstly be taken up by the cell. Only little is known with regard to this uptake. Hitherto, no genes are known in eukaryontes, which code for specific L-arabinose transporters. All hexose transporters tested for the pentose D-xylose have a much higher affinity to D-glucose than to D-xylose. For L-arabinose, a similar situation is assumed. Of all strains constructed hitherto, which can utilize pentoses (D-xylose or L-arabinose), a relatively slow growth is reported. Above all, the slow and poor uptake of the pentoses is named as a reason for this (Becker and Boles, 2003; Richard et al., 2002). In fermentations in a sugar mixture, consisting of D-glucose and D-xylose or D-glucose and L-arabinose, the sugars are not converted simultaneously. Due to the high affinity of the transporters for D-glucose, D-glucose is metabolized at first. A so-called Diauxic shift occurs. Only after the D-glucose is exhausted is the pentose converted in a second, distinctly slower growth phase (Kuyper et al., 2005a; Kuyper et al., 2005b). The absence of specific transporters for pentoses is given as an explanation.

Novel Specific L-arabinose Transporter from *P. stipitis*

For industrial applications, it would be ideal if the microorganism which was used could convert all the sugars present in the medium as far as possible simultaneously (Zaldivar et al., 2001). In order to achieve this, specific transporters for each sugar type would be of great benefit. None were known hitherto particularly for L-arabinose.

In this invention, the inventots succeeded in finding a specific L-arabinose transporter gene from the genome of *P. stipitis* with a test system (see examples). Genome fragments from *P. stipitis* are localized on the plasmids pAraT1 and pAraT7, which are responsible for a specific growth on L-arabinose but not on D-glucose, D-mannose or D-galactose medium. The observed low growth on D-galactose was not caused by the plasmids pAraT1 or pAraT7. This concerned only the weak growth of EBY.VW4000, the initial strain of MKY06, which was already reported by Wieczorke et al. (1999). The possibility that the obtained growth was caused by a genomic mutation in MKY06 was ruled out. After a selection for the loss of the plasmid of the *P. stipitis* gene bank by twice streaking on FOA medium, no further growth was established after again streaking on L-arabinose medium. Therefore, the growth originated from the plasmids of the *P. stipitis* gene bank (see examples). It was shown that the plasmids found code a transporter.

In a BLAST search with the recently published genome of *Pichia stipitis*, a 100% conformity with HGT2 was found. Due to its high homology to the high-affinity glucose transporter HGT1 of *Candida albicans*, HGT2 was annotated as putative high-affinity glucose transporter. When the sequence is examined with regard to the possible transmembrane domains, 12 transmembrane domains are obtained, which is typical for transporters. It is therefore surprising that it is a pentose transporter (arabinose transporter) and not a hexose transporter.

Furthermore, a multitude of experimental obstacles and difficulties had to be overcome in locating and providing the transporter according to the invention, which can also be seen in greater detail from the examples and figures.

In the initial strain EBY.VW4000, a total of 21 monosaccharide transporter genes had to be deleted.

Furthermore, TAL1 had to be genomically over-expressed in this strain.

The establishing of the optimum growth conditions for carrying out the screen proved to be very difficult and time-consuming.

The transporter according to the invention is the first described specific arabinose transporter of eucaryonts.

It is a heterologously expressed transporter which is at the same time functionally incorporated in the plasma membrane of *S. cerevisiae*, which is not necessarily to be expected.

Some reports exist with regard to the difficulties concerning heterologously expressed transporters, see on this subject Chapter 2 in the book "Transmembrane Transporters" (Boles, 2002) and the article by Wieczorke et al., 2003.

Further biomass with significant amounts of arabinose:

| Type of biomass | L-arabinose [%] |
|---|---|
| Switchgrass | 3.66 |
| Large bothriochloa | 3.55 |
| Tall fescue | 3.19 |
| Robinia | 3 |
| Corn stover | 2.69 |
| Wheat straw | 2.35 |
| Sugar can bagasse | 2.06 |
| Chinese lespedeza | 1.75 |
| Sorghum bicolor | 1.65 |

The arabinose transporter according to the invention is also of great importance for their utilization.

Possibilities for use of a functional and at the same time specific arabinose transporter in the yeast S. cerevisiae are on the one hand the production of bioethanol and the production of high-grade precursor products for further chemical syntheses.

The following list originates from the study "Top Value Added Chemicals From Biomass". Here, 30 chemicals were categorized as being particularly valuable, which can be produced from biomass.

| Number of C atoms | Top 30 Candidates |
|---|---|
| 1 | hydrogen, carbon monoxide |
| 2 | |
| 3 | glycerol, 3-hydroxypropionic acid, lactic acid, malonic acid, propionic acid, serine |
| 4 | acetoin, asparaginic acid, fumaric acid, 3-hydroxybutyrolactone, malic acid, succinic acid, threonine |
| 5 | arabitol, furfural, glutamic acid, itaconic acid, levulinic acid, proline, xylitol, xylonic acid |
| 6 | aconitic acid, citrate, 2,5-furandicarboxylic acid, glucaric acid, lysine, levoglucosan, sorbitol |

As soon as these chemicals are produced from lignocelluloses by bioconversion (e.g. fermentations with yeasts), it is important to have a specific transporter for the hemicellulose arabinose.

The present invention is further clarified in the following figures, sequences and examples, without however being restricted thereto. The cited references are fully included herewith by reference. In the sequences and figures there are shown:

SEQ ID NO: 1: the protein sequence encoded by the open reading frame (ORF) of AraT, SEQ ID NO: 2: the sequence of the open reading frame (ORF) of AraT, SEQ ID NO: 3: the sequence of the open reading frame (ORF) of AraT in a codon-optimized form, and SEQ ID NO: 4: the sequence of the open reading frame (ORF) of AraT with 500 promoter, ORF and 300 terminator.

The second most frequently occurring hemicellulose is a highly branched polymer consisting of pentoses, uronic acids and hexoses. The hemicellulose consists in a large proportion of the pentoses xylose and arabinose.

Figure 1:
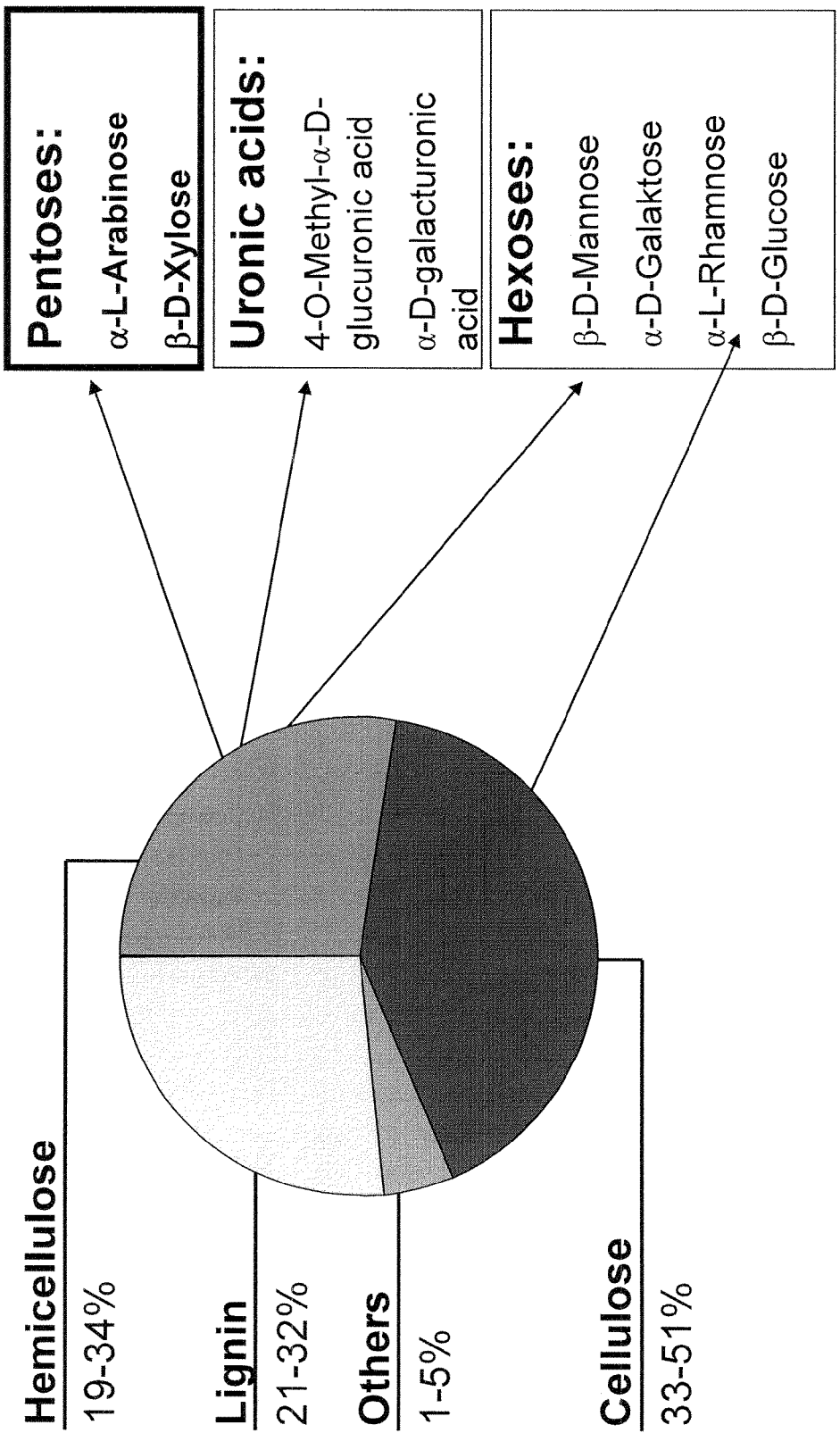
FIG. 1. Composition of the biomass
Figure 2:
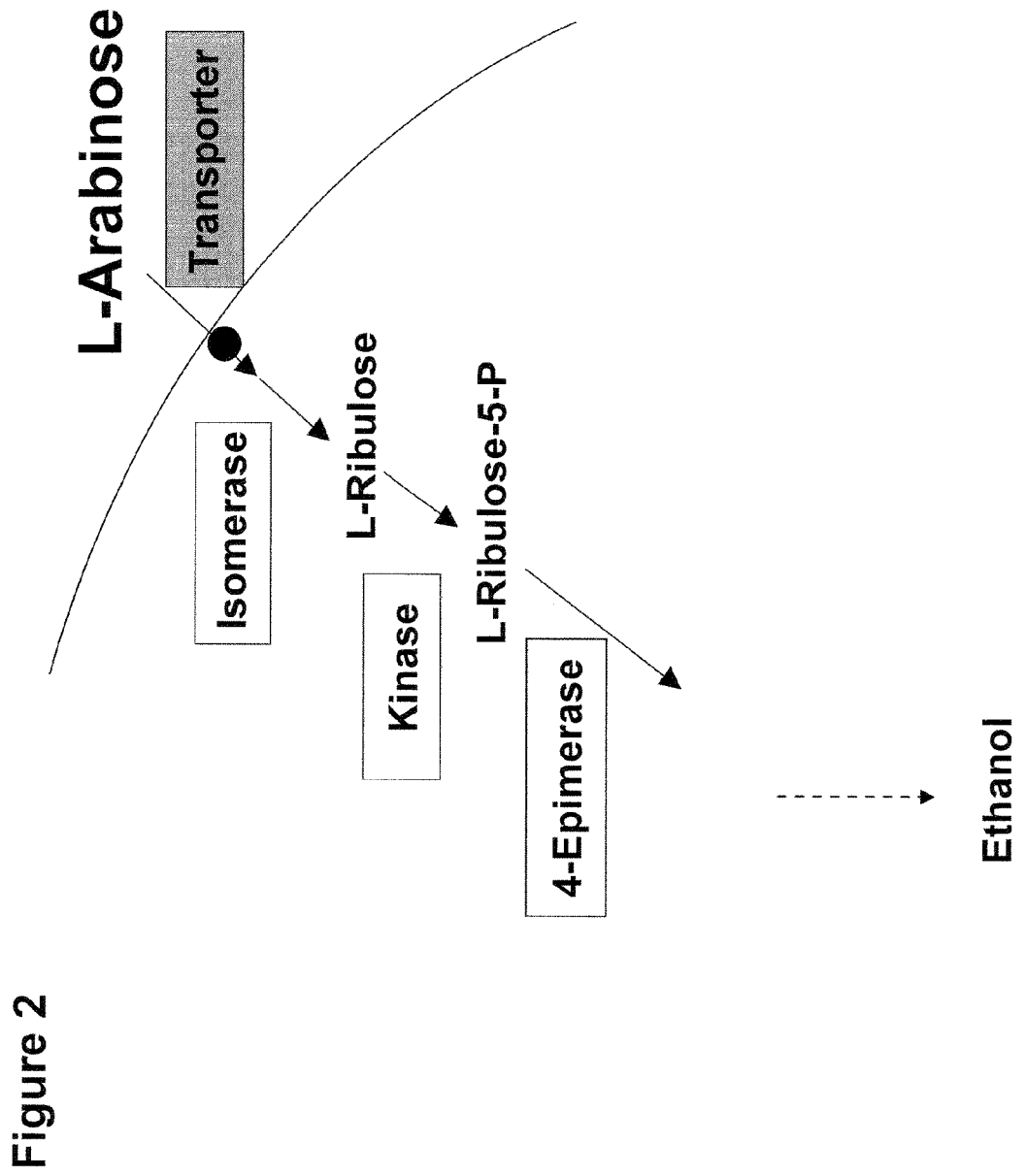

FIG. 2. Scheme for the use of L-arabinose in recombinant S. cerevisiae by integration of a bacterial L-arabinose metabolic pathway.

Figure 3:
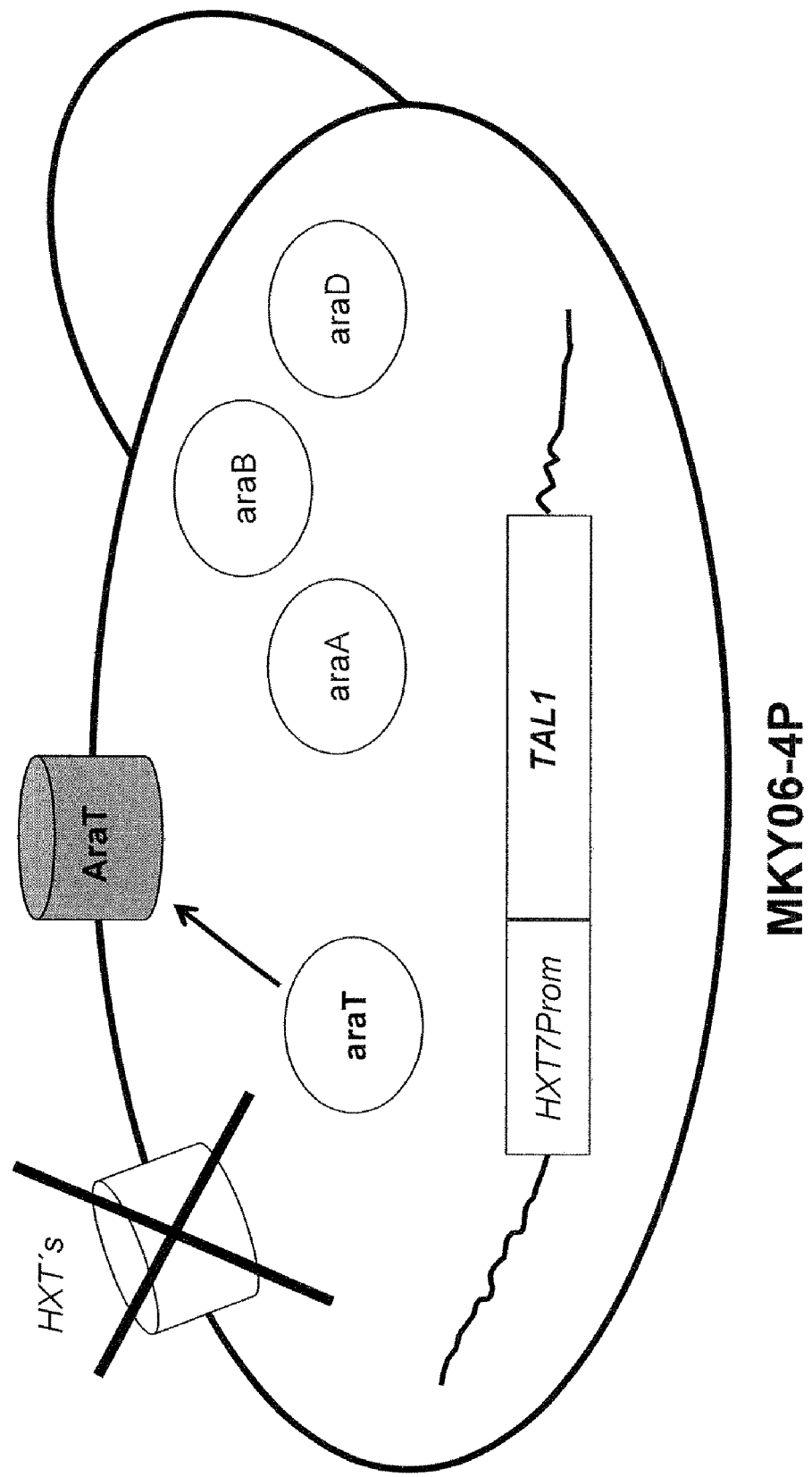

FIG. 3. Construction of the yeast strain MKY06-4P according to the invention.

The initial strain for the construction of MKY06-4P was the yeast strain EBY.VW4000, in which all hexose transporter genes (HCTs) were deleted. In this strain, the endogenous transaldolase TAL1 was over-expressed by the exchange of the native promoter for the shortened HXT7 promoter (HXT7-Prom). This led to the strain MKY06. Into this strain, the plasmids p423H7araABs$^{re}$ (araA), p424H7araB$^{re}$ (araB) and p425H7araD$^{re}$ (araD) were transformed for the arabinose metabolism (=MKY06-3P). In addition, the plasmid p426H7-araT (araT), which codes the arabinose transporter according to the invention from Pichia stipitis was also transformed into this strain and, thus, the strain MKY06-4P was obtained. The transporter is expressed and is functionally incorporated into the plasma membrane (AraT).

Figure 4A:
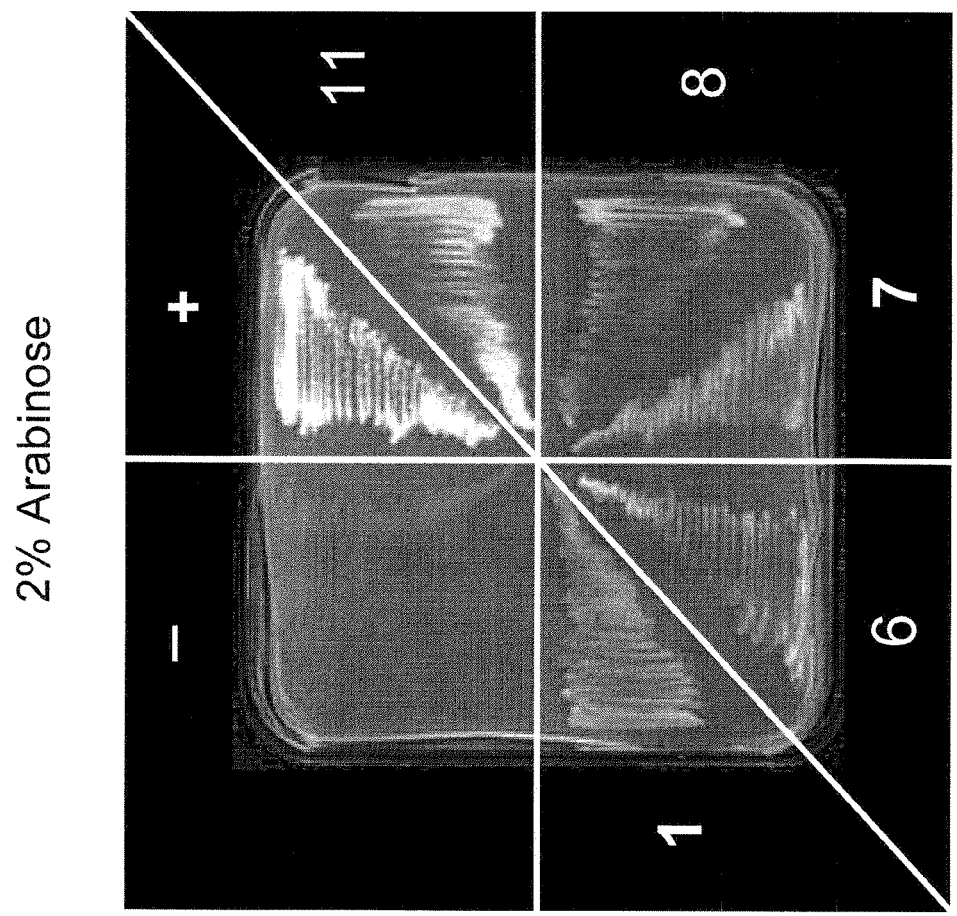
Figure 4B:
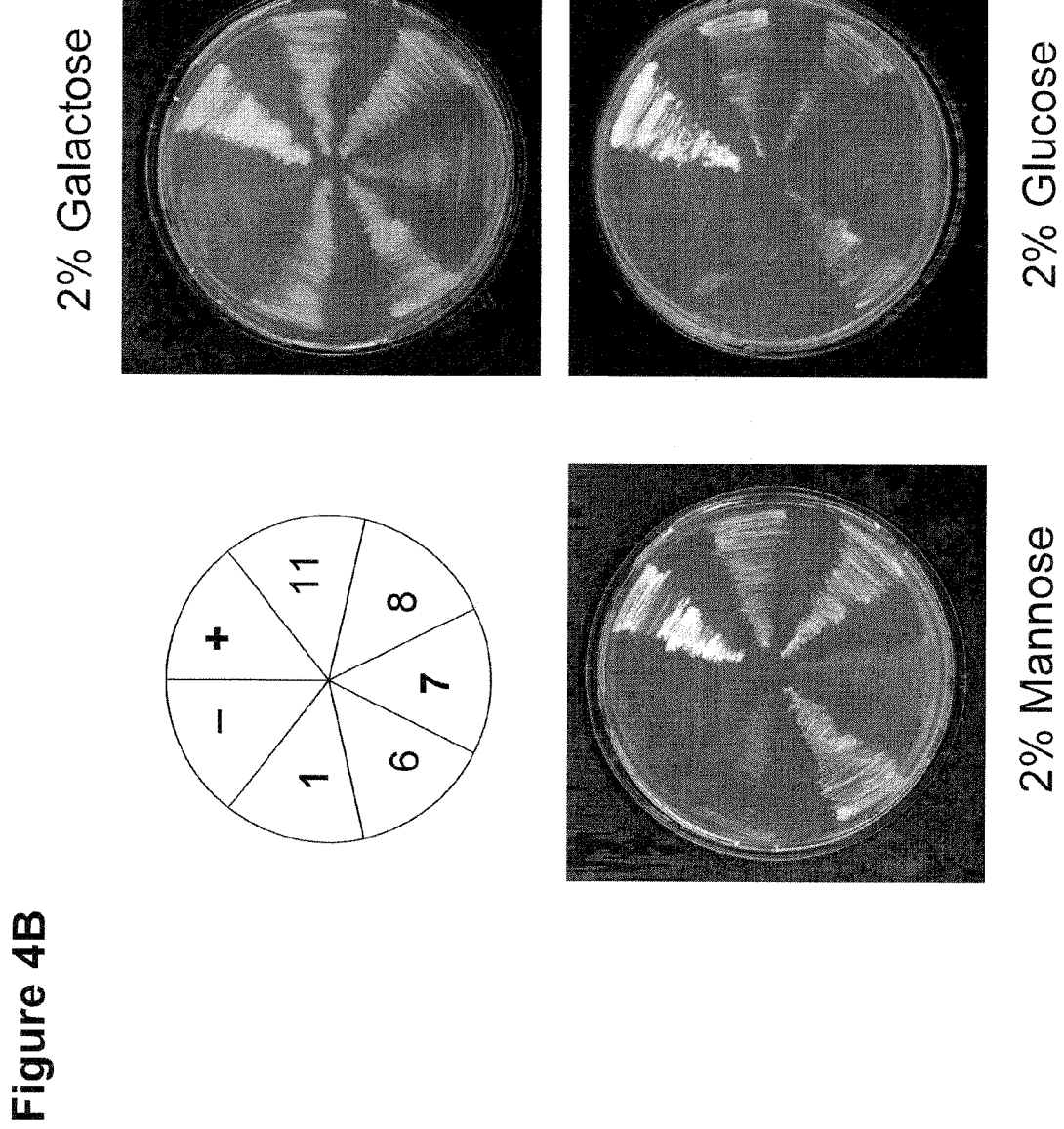

FIG. 4. Streaking on various carbon sources of MKY06 with the plasmids for the L-arabinose metabolism and the L-arabinose transporters found.

Each streak concerned the MKY06-3P and in addition a plasmid from the gene bank YEpTW. As a negative control (−), instead of a plasmid of the gene bank, p426HXT7-6HIS was transformed, and as positive control (+)pHL125 was transformed.

1: pAraT1,6:pAraT6,7:pAraT7,8:pAraT8,11:pAraT11, −: negative control, +: positive control.

A: Medium 2% L-arabinose

B: Medium 2% of each D-galactose, D-glucose or D-mannose

All SC medium plates were incubated at 30° C. The L-arabinose plate (A) shows growth after 9 days and all other plates (B) after 2 days. The colonies 1 and 7 grew on L-arabinose but not on D-glucose, D-mannose and only weakly on D-galactose.

Figure 5:
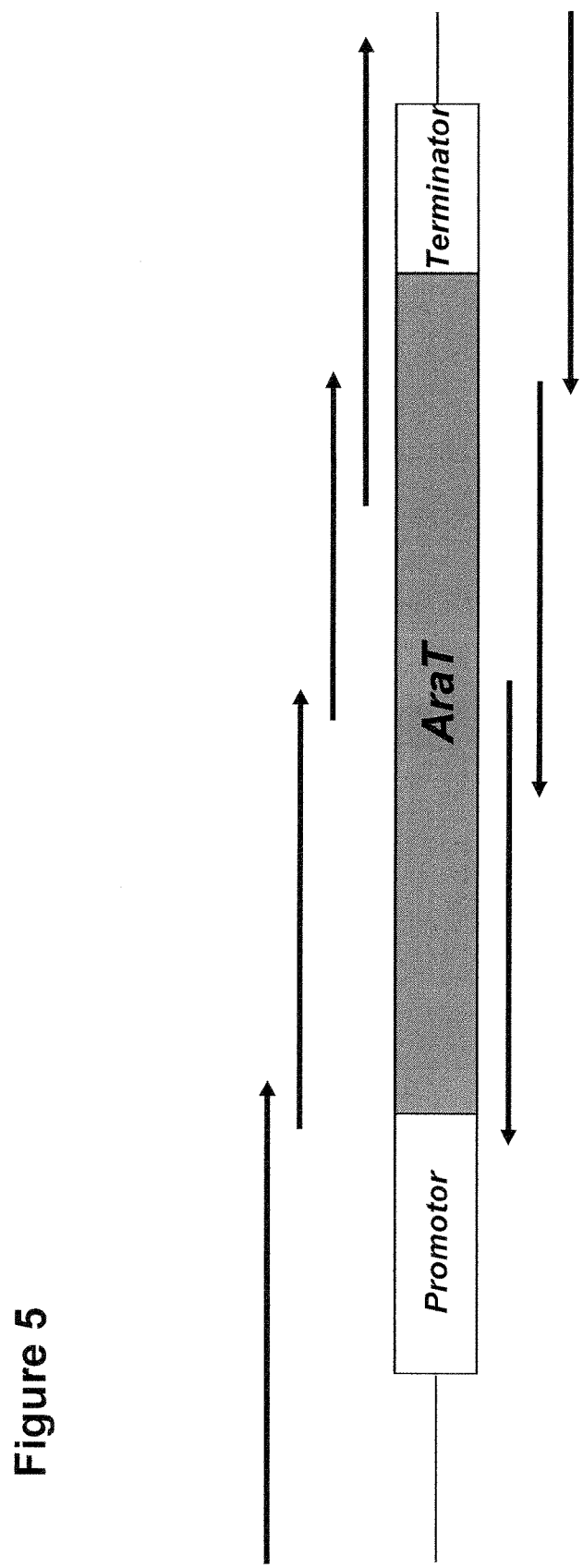
Figure 6A:
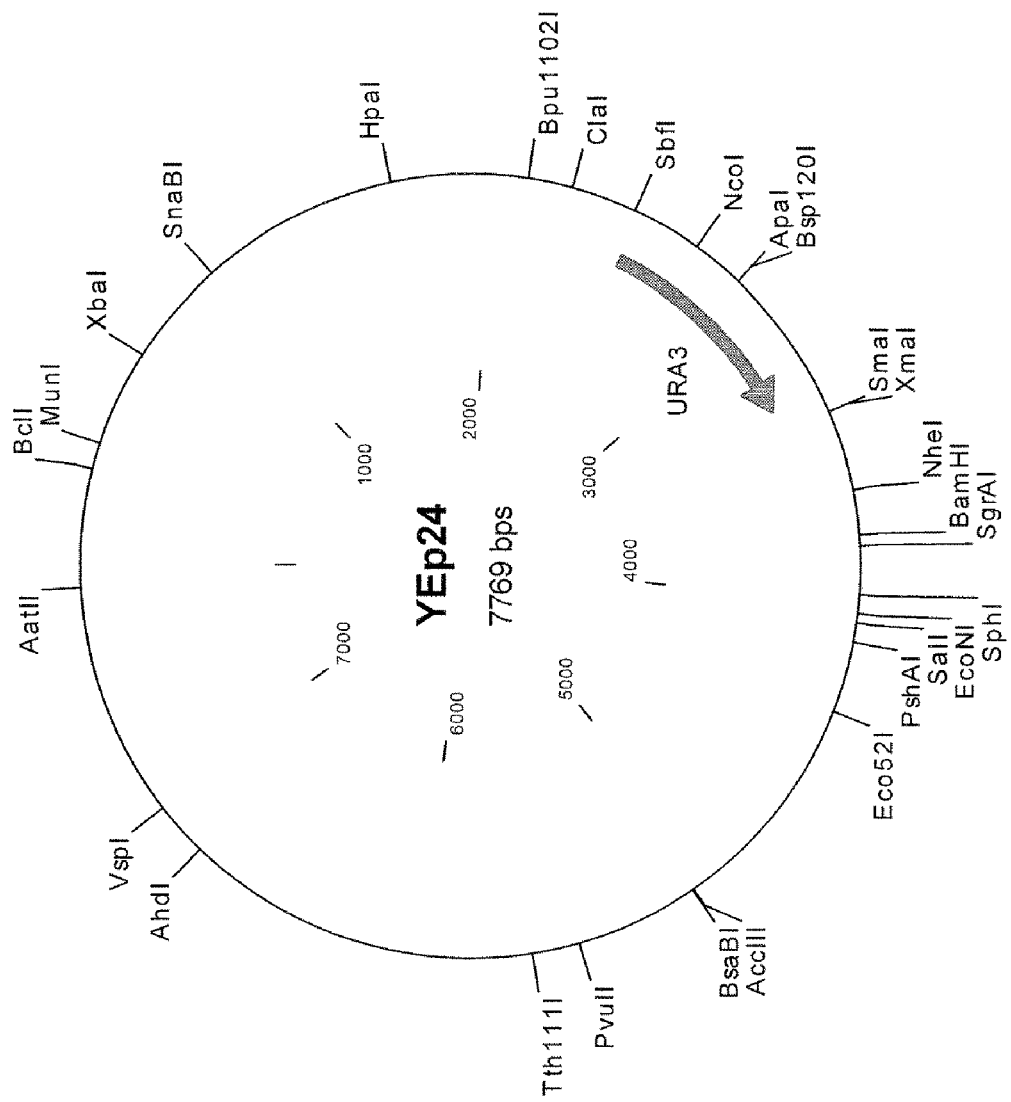
Figure 6B:
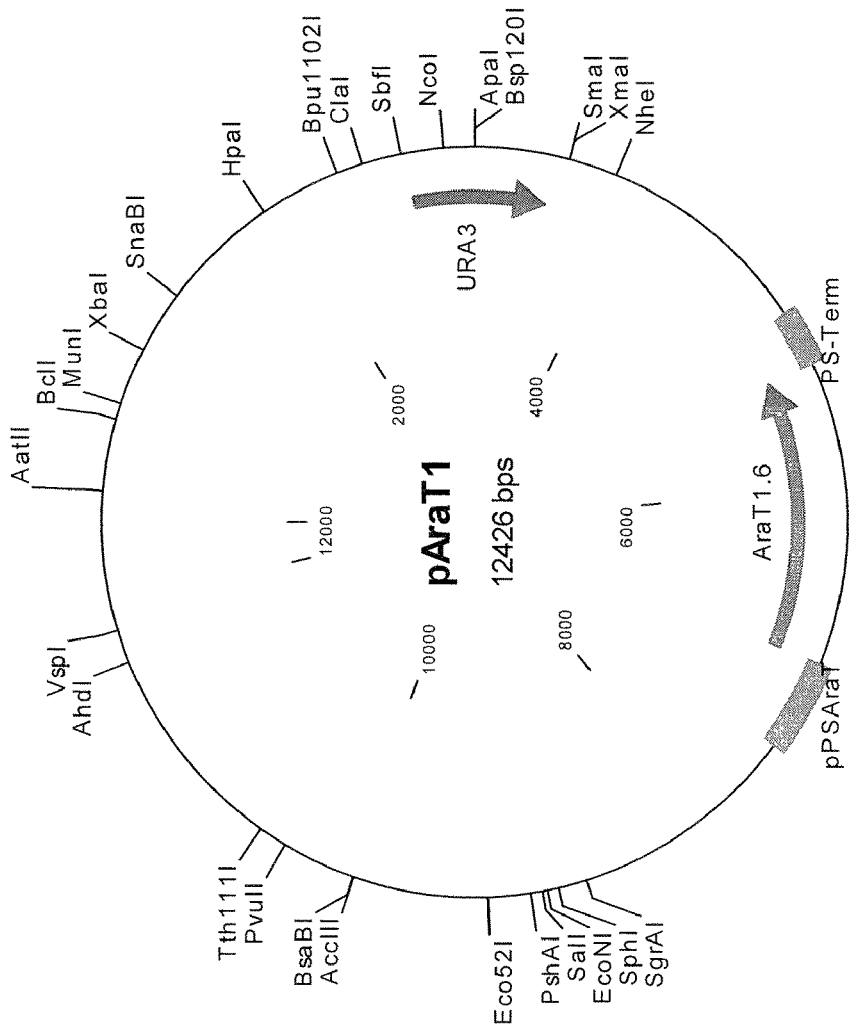
Figure 6C:
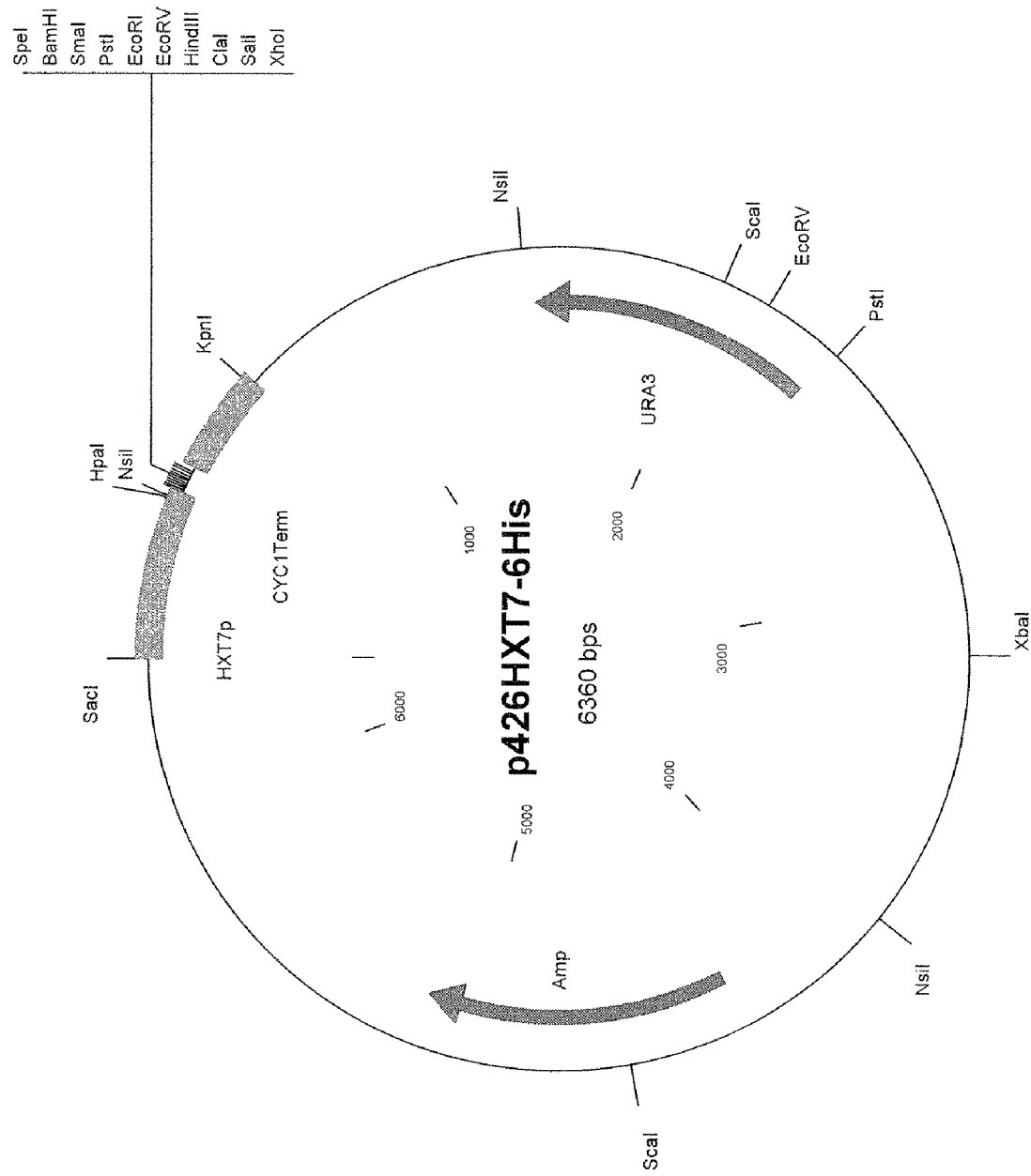
Figure 6D:
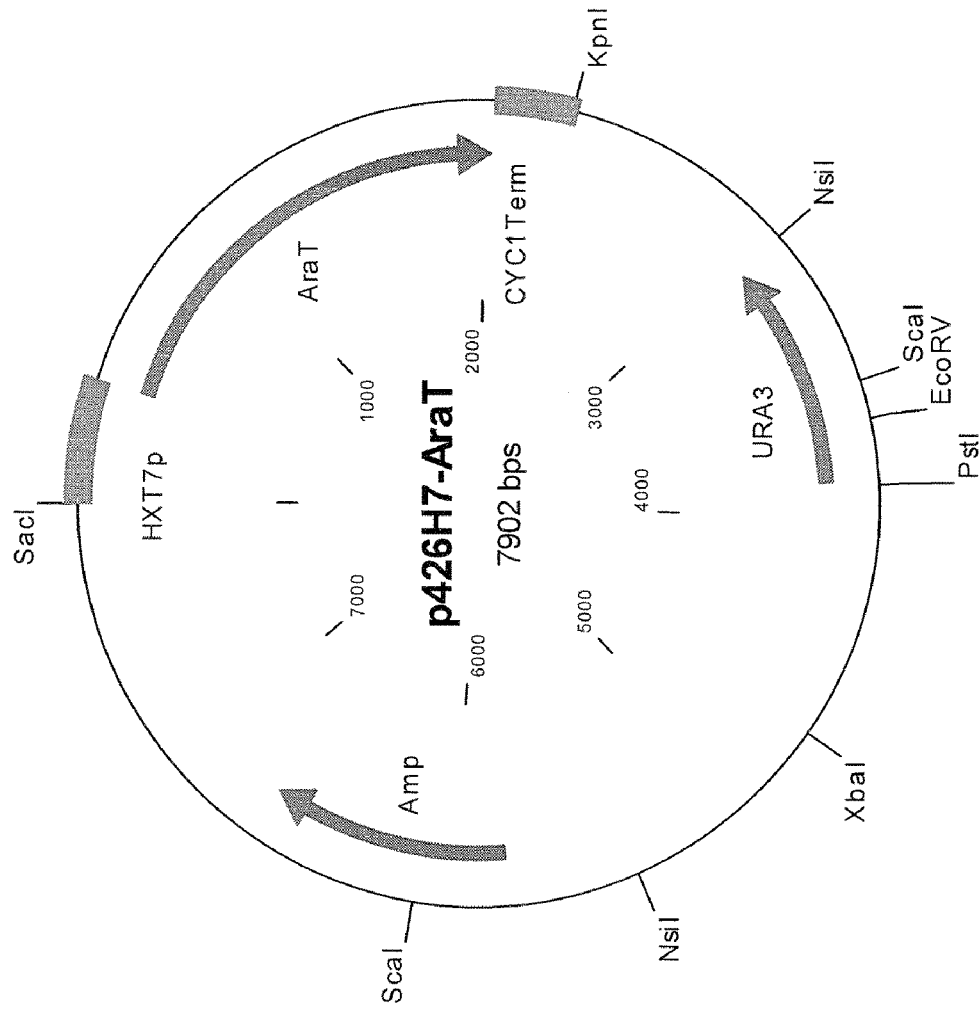
Figure 6E:
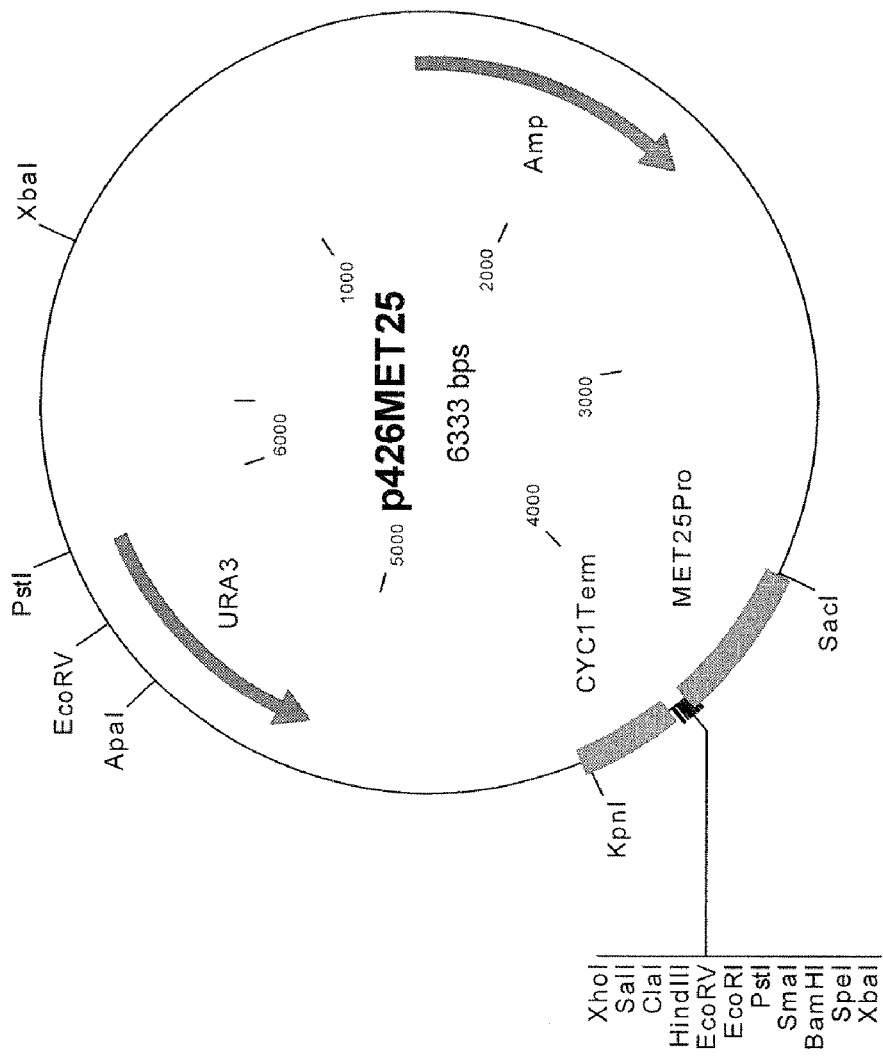

FIG. 5. Sequencing of the arabinose transporter.

The complete open reading frame of the transporter according to the invention was sequenced double-strand with overlapping regions. The promoter and terminator region was sequenced single-strand. The arrows indicate the regions of individual sequencings.

FIG. 6. Vectors used and their structure.

The initial plasmid for the production of the P. stipitis gene bank was the plasmid YEp24 (A). Both the plasmid pAraT1 (B) and the plasmid pAraT7 are therefore based on YEp24 and only differ in the size of the insert. The open reading frame (ORF) of the arabinose transporter according to the invention was amplified by the pAraT1 and was cloned after the shortened strong HXT7 promoter of the plasmid p426HXT7-6HIS (C). With this, the plasmid p426H7-AraT (D) was produced, which has a uracil marker. Another possible expression plasmid is p426Met25 (E).

FIG. 7. Growth on arabinose with the use of a specific arabinose transporter.

Growth of MKY06-3P, which additionally also contains the plasmid pHL125$^{re}$ or the plasmid p426H7-AraT (=MKY06-4P), in SM medium with A) 0.5%, B) 1% and C)

2% L-arabinose under aerobic conditions. The strains with the various plasmids were adducted in SM medium with 1% L-arabinose and inoculated with an $OD_{600nm}$=0.2 in 30 ml SM medium with A) 0.5%, B) 1% and C) 2% L-arabinose. The incubation took place in 300 ml shaking flasks under aerobic conditions at 30° C. Samples were taken several times in the day to determine the optical density.

Figure 8:
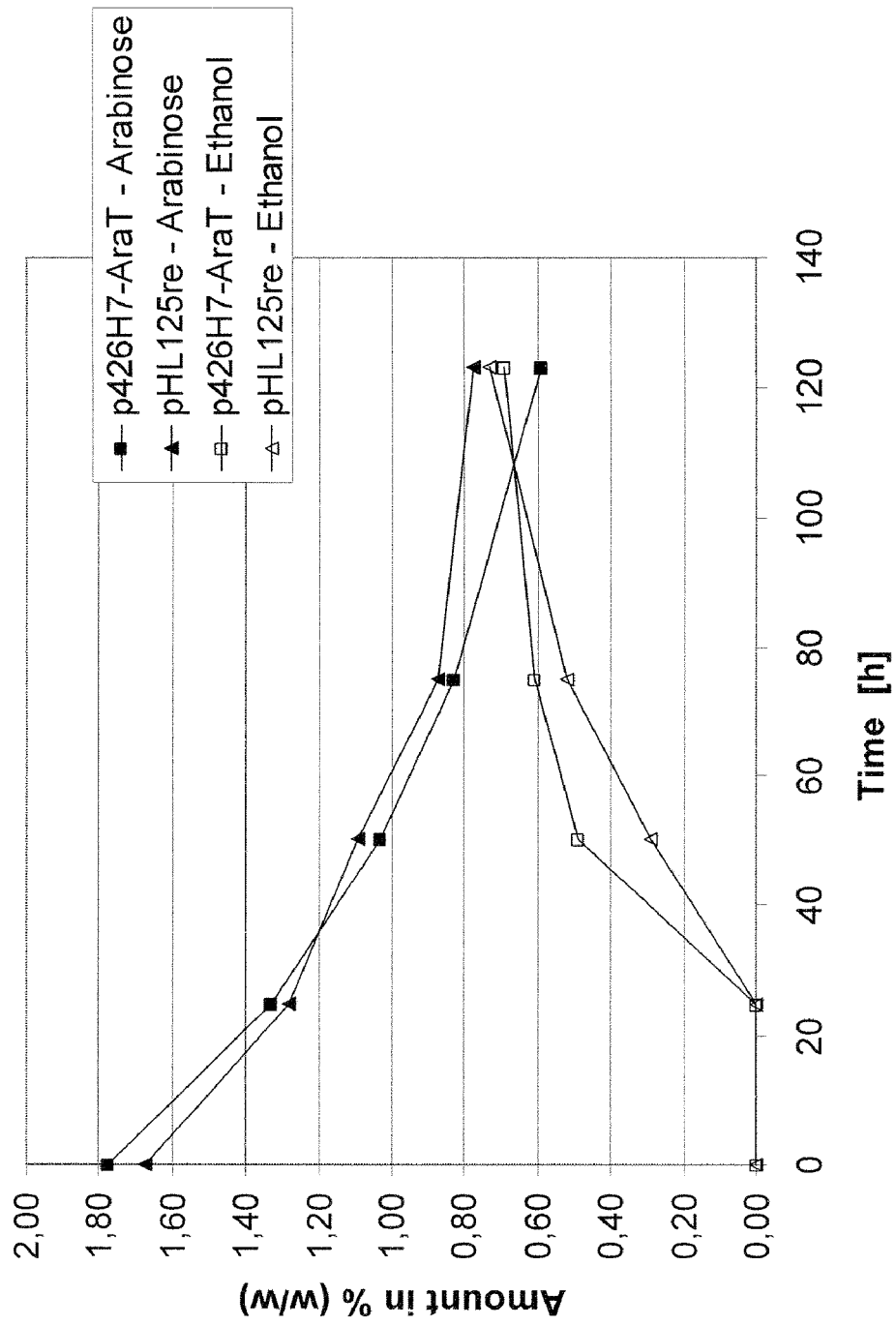

FIG. 8. Ethanol formation using a specific arabinose transporter

Shown are the results of HPLC analyses of the strain BWY1 with the plasmids p423H7araABs$^{re}$, p424H7araB$^{re}$, p425H7araD$^{re}$ and p426H7-AraT in SFM medium with 1.7% L-arabinose under semi-anaerobic conditions.

EXAMPLES

Methods

1. Strains and Media
Bacteria
*E. coli* SURE (Stratagene)
Full medium LB 1% trypton, 0.5% yeast extract, 0.5% NaCl, pH 7.5 (see Maniatis, 1982)
For selection on a plasmid-coded antibiotic resistance, 40 µg/ml ampicillin was added to the medium after autoclaving. Solid culture media additionally contained 1.9% agar. The culture took place at 37° C.
Yeast
Strain EBY.VW4000
EBY.VW4000 (Genotype: MATa leu2-3, 112ura3-52 trp1-289 his3-Δ1 MAL2-8c SUC2 Δhxt1-17Δgal2 stlΔ::loxP agt1Δ::loxP mph2Δ::loxP mph3Δ::loxP) (Wieczorke et al., 1999)
Strain MKY06
MKY06 (Genotype: MATa leu2-3,112 ura3-52 trp1-289 his3-MAL2-8c SUC2 hxt1-17 gal2 stl1::loxP agt1::loxP mph2::loxP mph3::loxP PromTAL1::loxP-Prom-vkHXT7, description: EBY.VW4000 PromTAL1::loxP-Prom-vkHXT7)
Strain MKY06-3P
MKY06-3P (Genotype: MATa leu2-3,112 ura3-52 trp-289 h is 3-1 MAL2-8c SUC2 hxt1-17 gal2 stl1::loxP agt1::loxP mph2::loxP mph3::loxP PromTAL1::loxP-Prom-vkHXT7, description: EBY.VW4000 PromTAL1::loxP-Prom-vkHXT7); contains the plasmids p423H7araABs$^{re}$, p424H7araB$^{re}$ and p425H7araD$^{re}$.
Strain with Accession Number DSM 18544
MKY06-4P (Genotype: MATa leu2-3,112 ura3-52 trp1-289 his3-1 MAL2-8c SUC2 hx1-17 gal2 stl1::loxP agt1::loxP mph2::loxP mph3::loxP PromTAL1::loxP-Prom-vkHXT7, description: EBY.VW4000 PromTAL1::loxP-Prom-vkHXT7); contains the plasmids p423H7araABs$^{re}$, p424H7araB$^{re}$, p4251-17araD$^{re}$ and p426H7-AraT.
Strain BWY1:
BWY1 is based on the strain JBY25 (Genotype: MATa leu2-3,112 ura3-52 trp1-289 his3-Δ1MAL2-8c SUC2+unknown mutations for better growth on L-arabinose) (Becker and Boles, 2003); the strain JBY25 was further selected and has still further mutations for improved growth on L-arabinose under oxygen-limited conditions (Wiedemann, 2005).
Full Medium YEP
1% yeast extract, 2% bacteriological peptone, carbon source in the respectively indicated concentration
Synthetic Complete Selective Medium SC
0.67% yeast nitrogen base w/o amino acids and ammonium sulphate, 0.5% ammonium sulphate, 20 mM potassium dihydrogenphosphate, pH 6.3, amino acid/nucleobase solution without the corresponding amino acids for the auxotrophy markers of the plasmids used, carbon source in the respectively indicated concentration Synthetic Minimal Selective Medium SM:
0.67% yeast nitrogen base w/o amino acids and ammonium sulphate, 0.5% ammonium sulphate, 20 mM potassium-dihydrogenphosphate, pH 6.3, carbon source in the respectively indicated concentration Synthetic Fermentation Medium (Mineral Medium) SFM (Verduyn at al., 1992), pH5.0

Salts: $(NH_4)_2SO_4$, 5 g/l; $KH_2PO_4$, 3 g/l; $MgSO_4 \cdot 7H_2O$, 0.5 g/l

Trace metals: EDTA, 15 mg/l; $ZnSO_4 \cdot 7H_2O$, 4.5 mg/l; $MnCl_2 \cdot 4H_2O$, 0.1 mg/l; $CoCl_2 \cdot 6H_2O$, 0.3 mg/l; $CuSO_4$ 0.192 mg/l; $Na_2MoO4 \cdot 2H_2O$, 0.4 mg/l; $CaCl_2 \cdot 2H_2O$, 4.5 mg/l; $FeSO_4 \cdot 7H_2O$, 3 mg/l; $H_3BO_3$, 1 mg/l; KI, 0.1 mg/l Vitamins: biotin, 0.05 mg/l; p-aminobenzoic acid, 0.2 mg/l; nicotinic acid, 1 mg/l; calcium pantothenate, 1 mg/l; pyridoxine-HCl, 1 mg/l; thiamine-HCl, 1 mg/l; m inositol, 25 mg/l Concentration of the amino acids and nucleobases in the synthetic complete medium (Zimmermann, 1975): adenine (0.08 mM), arginine (0.22 mM), histidine (0.25 mM), isoleucine (0.44 mM), leucine (0.44 mM), lysin (0.35 mM), methionine (0.26 mM), phenylalanine (0.29 mM), threonine (0.48 mM), tryptophan (0.19 mM), tyrosin (0.34 mM), uracil (0.44 mM) and valine (0.49 mM). As carbon sources, L-arabinose, D-glucose, D-galactose, D-mannose and maltose were used. For the selection on loss of a plasmid with URA3 selection marker gene, synthetic complete medium plates were used, which in addition to uracil contained 1 mg/ml 5-FOA, which was added after autoclaving (Boeke et al., 1984).

Solid full and selective media contained in addition 1.9% agar. The culture of the yeast cells took place at 30° C. The synthetic mineral medium used for the fermentation contained salts, trace metals and vitamins in the concentrations listed above and the indicated carbon source. A stock solution was prepared from the trace metals and the vitamins. The trace metal solution was autoclaved (20 min, 121° C.) and the vitamin solution was sterile-filtered. Both were stored at 4° C. The pH value had a decisive role for the production of the trace metal solution and prevented the precipitation of individual components. The various trace metals had to be completely dissolved in the above sequence in succession in water. After each addition, the pH value had to be adjusted with KOH to 6.0 before the next trace metal was able to be added. At the end, the pH value was adjusted with HCl to 4.0. In order to avoid foaming, 50 µl/l antifoam was added to the medium (Antifoam204, Sigma). In anaerobic experiments, in addition 2.5 ml/l of a Tween80-ergosterol solution was added to the medium after autoclaving. This consists of 16.8 g Tween80 and 0.4 g ergosterol, which were filled up to 50 ml with ethanol and dissolved therein. The solution was sterile-filtered. The salts, the corresponding quantities of trace metal solution and the antifoam were autoclaved together with the complete fermenter. The carbon source was autoclaved separately from the remaining medium. Before autoclaving, the pH was set to 5.0 in all. The sterile vitamin solution was added to the medium after cooling.

2. Plasmids

| Plasmid | Source/Reference | Description |
| --- | --- | --- |
| P423H7araABs$^{re}$ | Becker and Boles, 2003 | *B. subtilis* araA in p423HXT7-His, reisolated from JBY25-4M |
| P424H7araB$^{re}$ | Becker and Boles, 2003 | *E. coli* araB in p423HXT7-His; reisolated from JBY25-4M, mutation in araB |
| P425H7araD$^{re}$ | Becker and Boles, 2003 | *E. coli* araD in p425HXT7-His; reisolated from JBY25-4M |
| P426HXT7- | Becker and Boles, 2003 | 2µ plasmid for over-6HIS expression of genes and for production of fusion proteins with 6xHis-Epitope; URA3 marker gene, shortened HXT7 promoter and CYC1 terminator |
| pHL124$^{re}$ | Guldener et al., 1996 | 2µ plasmid with the GAL2 gene expressed behind the ADH1 promoter, URA3 marker gene, reisolated from JBY25-4M |
| P426H7-araT | | 2µ plasmid expressed with the *Pichia stipitis* ARAT behind the shortened HXT7 promoter, URA3 marker gene |

3. *Pichia stipitis* Gene Bank

YEpTW *Pichia stipitis*: Gene bank with chromosomal fragments of *Pichia stipitis* in the over-expression plasmid YEp24, URA3 marker gene (Weierstall et al., 1999)

4. Transformation

Transformation of *S. cerevisiae*

The transformation of *S. cerevisiae* was carried out by the lithium-acetate method (Gietz and Woods, 2002). For the selection on a geneticin resistance, the cells were incubated after the transformation for 4 h at 30° C. in full medium and subsequently plated on medium plates containing G418.

Transformation of *E. coli*

The transformation of the *E. coli* cells took place by the electroporation method (Dower et al., 1988; Wirth, 1993) by means of an Easyject prima apparatus from EQUIBO.

5. Preparation of DNA

Isolation of Plasmid-DNA from *S. cerevisiae*

The cells of a stationary yeast culture (5 ml) were harvested, washed and re-suspended in 100 µl buffer 1 (taken from the "Plasmid Mini Kit"). After the addition of 200 µl buffer 2 and ⅔ volume glass beads (diameter=0.45 mm), the cells were solubilised for 8 min on a Vibrax (Janke and Kunkel, Vibrax-VXR) at 4° C. The supernatant was mixed with 150 µl buffer 3 and incubated for 10 min on ice. After centrifuging for 15 minutes at 10000 R/min, the supernatant was used and the plasmid-DNA was precipitated with 400 µl isopropanol (−20° C., 10 min). The DNA, which was pelleted through centrifuging (30 min, 13000 rpm) was washed with 70% cold ethanol and held in 20 µl water. The DNA was then used for a transformation in *E. coli* or a DNA amplification by means of PCR.

Isolation of Plasmid-DNA from *E. coli*

The isolation of plasmid-DNA from *E. coli* took place with the "Plasmid Mini Kit" of the company Qiagen, according to the manufacturer's information.

Determining the DNA Concentration

The DNA concentration is measured by spectral photometry in a wavelength range of 240-300 nm. If the purity of the DNA, determined by the quotient E260 nm/E280 nm is 1.8, then the extinction E260 nm=1.0 corresponds to a DNA concentration of 50 µg dsDNA/ml (Maniatis, 1982).

6. DNA Amplification by Means of PCR

Use of the Expand™ High Fidelity System

The polymerase chain reaction (PCR) took place with the "Expand™ High Fidelity PCR System" of the company Roche, according to the manufacturer's information. 0.2 mM dNTP-mix, 1× buffer 2 (contains 1.5 mM MgC12), 1 U polymerase and 100 µmol each of the corresponding oligonucleotide primers were added together to the plasmid- or genomic DNA to be amplified. The PCR reaction was carried out in a thermocycler (Techne) or mastercycler (Eppendorf).

For the amplification of the DNA, the following temperature cycles were selected.

1. 1×95° C., 4 min denaturing of the DNA
2. 18-35×95° C., 45-60 sec denaturing of the DNA 55-60° C., 45-60 sec binding of the primers to the DNA (annealing) 72° C., 1-3 min DNA synthesis (elongation)
3. 1×72° C., 4 min synthesis (elongation)

After the first step, the polymerase was added ("hot start PCR"). The number of synthesis steps, the annealing temperature and the elongation time were adapted to the specific melting temperatures of the oligonucleotides which were used or to the size of the product which was to be expected. The PCR products were checked by a subsequent agarose gel electrophoresis and then purified.

DNA Purification of PCR Products

The purification of the PCR products took place with the "QIAquick PCR Purification Kit" of the company Qiagen, according to the manufacturer's information.

Gel Electrophoretic Separation of DNA Fragments

The separation of DNA fragments with a size of 0.15-20 kb took place in 1-4% agarose gels. 1×TAE buffer (40 mM Tris, 40 mM acetic acid, 2 mM EDTA) was used as gel- and running buffer (Maniatis, 1982). Serving as marker was either a lambda phage DNA cut with the restriction endonucleases EcoRI and HindIII, or the 2-log DNA ladder (NEB). Before application, the DNA samples were mixed with 1/10 volume blue marker (1×TAE buffer, 10% glycerine, 0.004% bromophenol blue). After the separation, the gels were incubated in an ethidium bromide bath and the DNA fragments were made visible by irradiation with UV light (254 nm).

Isolation of DNA Fragments from Agarose Gels

The desired DNA fragment was cut out from the TAE agarose gel under longwave UV light (366 nm) and isolated with the "QIAex II Gel Extraction Kit" or the "QIA-quick Gel Extraction Kit" of the company Qiagen, according to the manufacturer's information.

7. Enzymatic Modification of DNA

DNA restriction

Sequence-specific splittings of the DNA with restriction endonucleases were carried out under the incubation conditions recommended by the manufacturer for 2-3 hours with 2-5U enzyme per µg DNA.

8. HPLC Analyses

The samples taken in the tests were centrifuged for 10 min at 3000 R/min, in order to pellet the yeast cells. The supernatant was removed and immediately frozen at −20° C. For the protein precipitation, subsequently 50% sulphosalicylic acid was added, mixed, and centrifuged off for 30 min at 13000 R/min and 4° C. The supernatant was removed, a 1/10 dilution with water was produced therefrom and used for the HPLC analyses. Serving as standards for the measurements were samples with D-glucose, L-arabinose, and ethanol, which were used in concentrations of 0.1% w/w, 0.5% w/w and 1.0% w/w. The sugar- and ethanol concentrations were measured by means of BioLC (Dionex). The autosampler "AS50", the column oven "TCC-100", the gradient pump "GS50" (all Dionex) and the RI detector "RI-101" (Shodex)

were used in the measurement. As a column, the VA 300/7.7 nucleogel sugar 810H (Machery-Nagel) was used with 20% sulphuric acid as eluent (0.6 ml/min). For the evaluation of the analysis data, the Chromeleon™ program (Version 6.50, Dionex) was used.

Example 1

Design of a Test System for the Examination of L-arabinose Transporters

A) Construction of the MKY06

In the yeast strain EBY.VW4000 all the genes of the hexose transporter family and in addition three genes of the maltose transporter family were deleted. This strain grew on maltose medium unchanged, but was no longer able to grow on glucose, fructose and mannose and only very weakly on galactose (Wieczorke et al., 1999). As all hexose transporters are deleted, it can be assumed that the strain also can no longer receive any L-arabinose and is therefore suitable for arabinose transport investigations.

In preceding tests (see Becker and Boles, 2003), it had been found that in addition to a functional L-arabinose metabolic pathway, also an increased activity of transaldolase was necessary for the use of L-arabinose. For this reason, by exchange of the endogenous promoter of TAL1 in EBY.VW4000 for the shortened HXT7 promoter TAL1 was over-expressed. This strain was named MKY06 and is provided, with the plasmids for the L-arabinose metabolism and a transporter which can transport L-arabinose, to grow on this carbon source.

B) Introduction of the L-arabinose Metabolic Pathway

The strain MKY06 was transformed with the plasmids p423H7araABs$^{re}$, p424H7araB$^{re}$ and p425H7araD$^{re}$ (=MKY06-3P), so that it obtains the capability of L-arabinose use. The transformation with the three plasmids took place simultaneously. The transformants were plated on medium with 2% maltose. In a further transformation, as positive control in addition the transporter Gal2, known as L-arabinose, was transformed in and as negative control the empty plasmid p426HXT7-6HIS and plated again on medium plates containing maltose. The positive control, which contains an L-arabinose transporter and the three plasmids for the L-arabinose use and over-expresses transaldolase, should be able to grow on L-arabinose. The negative control should show no growth owing to the absent transporter. This was investigated.

C) Checking the Test System

In order to be able to use the constructed test system further, firstly the positive and negative controls had to be investigated with regard to their growth. Several colonies of the transformants obtained on the SC plates with 2% maltose were removed with a sterile inoculating loop and smeared on SC plates with 2% L-arabinose and incubated at 30° C. for ten days. After this time, the positive control showed a distinct growth and the negative control, as expected, showed no growth.

The growth behaviour was likewise investigated in liquid medium with 2% maltose or 2% L-arabinose. For this, precultures were adducted with the corresponding carbon sources (maltose or L-arabinose) under aerobic conditions at 30° C. After reaching the late exponential phase, these precultures were used in order to inoculate 30 ml of the same medium with an initial $OD_{600nm}$=0.2. As the negative control did not grow on medium plates containing L-arabinose, starting from the preculture with 2% maltose 30 ml SC medium was inoculated with 2% L-arabinose. The growth behaviour was followed over several days by measurement of the optical density at 600 nm. In the maltose medium, the positive and negative control showed identical growth, as expected, with a growth rate of 0.197 h$^{-1}$. In L-arabinose growth, precisely as already in the tests with the L-arabinose medium plates, growth was only found in the positive control ($\mu$=0.01 h$^{-1}$), which still had the transporter Gal2 compared with the negative control. The low growth at the start in the negative control can be explained in that before the reinoculation of maltose the cells were not grown on medium containing L-arabinose. In addition, the glycogen stores of the yeast make still make a slight growth possible.

This test system was therefore functional and was able to be used for the investigation of L-arabinose transporters. The positive and negative control mentioned here always served as a comparison in this.

Example 2

Screen with a *Pichia stipitis* Gene Bank

The test system was now used in order to seek in a gene bank of *Pichia stipitis* one of the yeasts which can use L-arabinose, for possible L-arabinose transporter genes.

A) Carrying Out the Screen

The gene bank YEpTW which was used here was produced form the *Pichia stipitis* strain CBS5774. Chromosomal DNA was partially digested with the restriction endonuclease Sau3A and ligated into the vector Yep24 linearised with BamHI (Weierstall et al., 1999).

The gene bank, exactly like the plasmid pHL125$^{re}$, had a uracil auxotrophy marker. The gene bank YEpTW was transformed into the strain MKY06-3P and smeared on SC medium with 2% maltose. The colonies obtained after three days at 30° C. were replica-plated on SC medium plates with 2% L-arabinose. After 10 days, colonies were sought which showed growth on L-arabinose. Growth was only possible when the plasmid of the gene bank coded a transporter which was able to transport L-arabinose.

In order to be able to rule out genomic mutations which could be responsible for the growth, the colonies which were found were smeared on complete medium with 5-FOA. Thereby, selection was carried out on a loss of the plasmid of the gene bank. With renewed smearing on L-arabinose medium, these colonies of the 5-FOA plate were no longer able to grow hereon. Therefore, a genomic mutation was able to be ruled out as the cause of the growth. The colonies which were found were also smeared on other carbon sources, in order to test the substrate spectrum.

B) Growth Behaviour

Of the over 30000 replica-plated colonies, the eleven colonies found here which showed slight growth were smeared again on L-arabinose plates. Here, however, only five colonies showed growth again on L-arabinose. This was the strain MKY06-3P, which additionally contained the plasmid pAra1, pAraT6, pAraT7, pAraT8 or pAraT11 from the gene bank YEpTW (see FIG. 4). The strongest growth was shown by MKY06-30 with pAraT11. The others grew more weakly compared with the positive control. However, it must be taken into account here that the GAL2 in the positive control was over-expressed by a strong promoter and the genes on the plasmids of the gene bank had their native promoter. The plasmids pAraT1 and pAraT7 are of particular interest, because these only presented growth on L-arabinose medium. These showed no growth on D-glucose and on D-mannose. On D-galactose, pAraT1 only brought about slight growth. The growth of pAraT7 on D-galactose corresponded to the weak growth of the negative control (cf. FIG. 4). This was already reported earlier for the initial strain of MKY06, EBY.VW4000 (Wieczorke et al., 1999).

The colonies with pAraT6, pAraT7 and pAraT11 were adducted in liquid SC medium with 2% L-arabinose and glycerine cultures were prepared herefrom, which are stored for later investigations at −70° C. Further work was carried out with the plasmids pAraT1 and pAraT7 and the growth behaviour of the strains was investigated in liquid medium. In SC medium with 2% maltose, the MKY06-3P, which additionally contained pAraT1 or pAraT7, behaved identically to the positive- (additionally also pHL125$^{re}$) and the negative control (additionally also p426HXT7-6HIS). The growth rates were 0.197 h$^{-1}$.

Differences were found on SC medium with 2% L-arabinose. The negative control (p426HXT7-6HIS) showed no growth on this medium. The slight growth at the start resulted from the absent washing step in the reinoculation from the preculture on maltose medium to the main culture in L-arabinose medium. Both L-arabinose transporters which were found behaved similarly. In the growth rate ($\mu$=0.087 h$^{-1}$) and also in the maximum OD$_{600nm}$ there were no differences between the MKY06-3P with the plasmid pAraT1 or the pAraT7. If one compares the growth behaviour of the two new transporters with the positive control (pHL125$^{re}$, $\mu$=0.1 h$^{-1}$, then a somewhat lower growth rate and a lower maximum OD$_{600nm}$ are found.

C) Isolation of the L-arabinose Transporters which were Found

In order to be able to analyse the transporters which were found on a genomic level, firstly the gene bank plasmids had to be isolated again from the yeast. It was to be noted here that the strain MKY06 not only contains the plasmid from the gene bank YEpTW, which codes the sought transporter, but at the same time also contains the three plasmids for the L-arabinose metabolism (p423H7araABs$^{re}$, p424H7araB$^{re}$, p425H7araD$^{re}$) and that the plasmid p423H7araABs$^{re}$ is present in a much higher number in the cells than the other three plasmids. As the plasmids of the gene bank YEpTW had a uracil auxotrophy marker, the cells were inoculated starting from the L-arabinose plates in maltose medium without uracil (ura-). After reaching the stationary phase, these were reinoculated into fresh maltose-ura medium and adducted again. Here, the cells were adducted with the four plasmids five times in maltose-ura liquid medium up to the stationary phase. The aim of this was an enrichment of the plasmid pAraT1 or pAraT7. From these two cultures, separation smears were prepared on maltose-ura medium plates. The colonies which were produced were replica-plated onto further maltose plates and incubated for two days at 30° C. These plates did not contain the corresponding amino acid for the auxotrophy marker of one of the other three plasmids (histidine for p423H7araABs$^{re}$, tryptophan for p424H7araB$^{re}$ or leucine for p425H7araD$^{re}$). These replica plates were compared with the maltose-ura plates. Colonies which only grew on the maltose-ura plate were selected. These only had the plasmid pAraT1 or pAraT7. The plasmids were isolated from yeast. Thereafter, the plasmids were amplified in *E. coli*, and after the isolation from *E. coli* were characterized by means of a restriction analysis. NcoI and NheI were used as restriction enzymes. NcoI only cuts in the URA3 marker gene. When the sought plasmid from the gene bank is concerned, then a 934 bp large fragment occurs.

Example 3

Characterization of the Novel Arabinose Transporter (araT)

A) Sequencing

The chromosomal fragments from *P. stipitis* localized on the plasmids pAraT1 and pAraT7 found in Example 2 were sequenced.

The complete ORF of the transporter which was found was double-strand sequenced with overlapping regions. The promoter and terminator region was single-strand sequenced (cf. FIG. 5). The arrows indicate the regions of individual sequencings.

In the sequencing it was found that the two plasmids pAraT1 and pAraT7 contain overlapping fragments of the same gene. This concerns one and the same transporter and not two different transporter genes. The plasmid pAraT1 has an insert with approximately 5 kb; it contains the complete open reading frame (ORF) of AraT, which consists of 1629 bases and consequently 542 amino acids (plus the STOP codon). Additionally also promoter- and terminator sequences. The plasmid pAraT7 has an insert which is approximately 3 kb in size; it does not contain the complete ORF of AraT, but rather only the first 1507 bases. Nevertheless, this fragment was, however, functional.

In a BLAST search with the recently published genome of *Pichia stipitis* a 100% conformity with HGT2 was found. HGT2 was annotated as putative high-affinity glucose transporter owing to its high degree of homology to the high-affinity glucose transporter HGT1 of *Candida albicans*. When one examines the sequence with regard to the possible transmembrane domains, one obtains 12 transmembrane domains, which is typical for transporters.

B) Examples for Vectors for AraT

The initial plasmid for the production of the gene bank was the plasmid YEp24. The plasmid pAraT1 and also the plasmid pAraT7 are therefore based on YEp24 and differ only in the size of the insert. The vector YEp24 is an episomal plasmid.

The open reading frame (ORE) of the arabinose transporter which was found was amplified by pA-raT1 and cloned behind the shortened strong HXT7 promoter of the plasmid p426HXT7-6HIS. With this, the plasmid p426H7-AraT was produced, which has a uracil marker.

Another possible expression plasmid is p426Met25. For vector maps, see FIGS. 6A to 6E.

Further possible expression vectors are pYES260, pYES263, pVTU260, pVTU263, pVTL260 and pVTL263.

C) Growth in Dependence on the L-arabinose Concentration in the Medium

The growth of the strain MKY06-4P was investigated under aerobic conditions as a function of the L-arabinose concentration in the medium. As a comparison, the strain MKY06-3P was used, which additionally also contained the plasmid pHL125$^{re}$ or p426HXT7-6HIS.

The strains with the various plasmids were adducted in SM medium with 1% L-arabinose and inoculated with an OD$_{600nm}$=0.2 in 30 ml SM medium with 0.5%, 1% or 2% L-arabinose. The incubation took place in 300 ml shaking flasks under aerobic conditions at 30° C. Samples were taken several times in the day to determine the optical density.

Figure 7B:
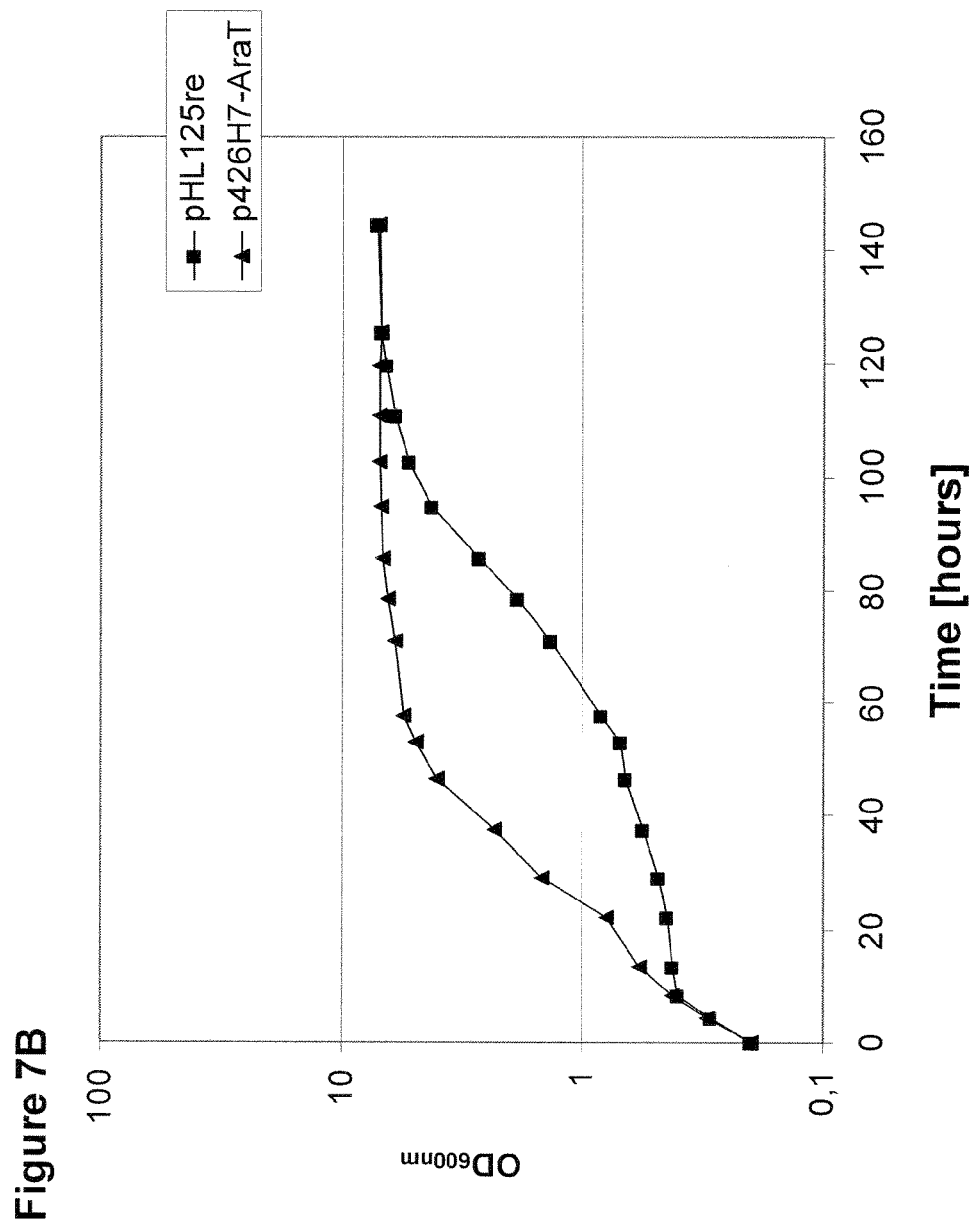

The results are shown in FIGS. 7A to 7C. The strain MKY06-4P grows under all 3 conditions more quickly than the comparative strain MKY06-3P, which still contains the plasmid pHL125$^{re}$. With 0.5% L-arabinose (FIG. 7A) a distinct advantage of p426H7-AraT is shown compared with pHL125$^{re}$. The strain grows distinctly more quickly and also to a higher optical density. Also with 1% L-arabinose (FIG. 7B) the strain grows with p426H7-AraT more quickly than the comparative strain. In the optical density reached at the end of growth, however, not difference is shown. Also with an L-arabinose concentration of 2% (FIG. 7C) the strain with p426H7-AraT grows more quickly than the comparative strain with pHL125$^{re}$ which, however, reaches a higher optical density at the end of growth with this concentration.

It is therefore shown that the L-arabinose uptake system according to the invention makes it possible for the recombinant *S. cerevisiae* cells to use L-arabinose substantially more efficiently.

Example 4

Use of The Novel Arabinose Transporter (araT) for the Formation of Ethanol

In FIG. 8 the results are shown of HPLC analyses of the strain BWY1 with the plasmids p423H7araABs$^{re}$, p424H7araB$^{re}$, p425H7araD$^{re}$ and in addition p426H7-AraT or as comparison pHL125$^{re}$ in SFM medium with 1.7% arabinose under semi-anaerobic conditions.

The strains were adducted aerobically in the same medium to a high optical density. The cells were centrifuged off and used for the inoculation of the semi-anaerobic fermentation tests. Already after approximately 25 hours, ethanol production begins in both strains. In the strain which contains the plasmid p426H7-AraT a higher ethanol production is able to be established at the start. On the other hand, the arabinose concentration at the end of the test decreases more strongly in the case of cells with p426H7-AraT than with pHL125$^{re}$, which indicates that here a higher affinity of AraT leads to an improved fermentation of low arabinose concentrations.

REFERENCES

Becker. J. and Boles, E. (2003) A modified *Saccharomyces cerevisiae* strain that consumes L-Arabinose and produces ethanol. *Appl Environ Microbiol* 69(7), 4144-50.

Boeke, J. D., LaCroute, F. And Fink, G. R. (1984) A positive selection for mutants lacking oritidine-5'-phosphate decarboxylase activity in yeast: 5-fluoroorotic acid resistance. *Mol Gen Genet.* 197(2), 345-6.

Boles, E. (2002) in "Transmembrane Transporters", Editor Michael W. Quick, WILEY-LISS, 19-36.

Burke, D., Dawson, D., Stearns, T. (2000) *Methods in Yeast Genetics. A Cold Spring Harbor Laboratory Course Manual.* Cold Spring Harbor Laboratory Press.

Dien, B. S., Kurtzman, C. P., Saha, B. C. and Bothast, R. J. (1996) Screening for L-arabinose fermenting yeasts. *Appl Biochem Biotechnol* 57-58, 233-42.

Dower, W. J., Miller, J. F. and Ragsdale, C. W. (1988) High efficiency transformation of *E. coli* by high voltage electroporation. *Nucleic Acids Res* 16(13), 6127-45.

Du Preez, J. C., Bosch, M. and Prior, B. A. (1986) Xylose fermentation by *Candida shehatae* and *Pichia stipitis*-effects of pH, temperature and substrate concentration. *Enzyme Microb Technol* 8(360-364).

Gietz, R. D. and Woods, R. A. (2002) Transformation of yeast by lithium acetate/single-stranded carrier DNA/polyethylene glycol method. *Methods Enzymol* 350, 87-96.

Hahn-Hagerdal, B., Wahlbom, C. F., Gardonyi, M., van Zyl, W. H., Cordero Otero, R. R. and Jonsson, L. J. (2001) Metabolic engineering of *Saccharomyces cerevisiae* for xylose utilization. *Adv Biochem Eng Biotechnol* 73, 53-84.

Jeppson M, Bengtsson O, Franke K, Lee H, Hahn-Hagerdal B, Gorwa-Grauslund M F. (2006) The expression of a *Pichia stipitis* xylose reductase mutant with higher K(M) for NADPH increases ethanol production from xylose in recombinant *Saccharomyces cerevisiae*. *Biotechnol Bioeng.* 93(4):665-73.

Jin Y S, Jeffries T W. (2004) Stoichiometric network constraints on xylose metabolism by recombinant *Saccharomyces cerevisiae*. *Metab Eng.* 6(3):229-38.

Katahira S, Mizuike A, Fukuda H, Kondo A. (2006) Ethanol fermentation from lignocellulosic hydrolysate by a recombinant xylose- and cellooligosaccharide-assimiliating yeast strain. *Appl Microbiol Biotechnol.* 72(6):1136-43.

Kotter, P. and Ciriacy, M. (1993) Xylose fermentation by *Sacharomyces cerevisiae*. *Appl Microbiol Biotechnol* 38, 776-783.

Kou, S. C., Christensen, M. S, and Cirillo, V. P. (1970) Galactose transport in *Saccharomyces cerevisiae*. II. Characteristics of galactose uptake and exchange in galactokinaseless cells. *J Bacteriol* 103(3), 671-8.

Kuyper, M., Toirkens, M. J., Diderich, J. A., Winkler, A. A., van Dijken, J. P. and Pronk, J. T. (2005b) Evolutionary engineering of mixed-sugar utilization by a xylose-fermenting *Saccharomyces cerevisiae* strain. *FEMS Yeast Res* 5(10), 925-34.

Kuyper, M., Winkler, A. A., van Dijken, J. P. and Prank, J. T. (2004) Minimal metabolic engineering of *Saccharomyces cerevisiae* for efficient anaerobic xylose fermentation: a proof of principle. *FEMS Yeast Res* 4(6), 655-64.

Lucas, C. and Uden, N. v. (1986) Transport of hemicellulose monomers in the xylose-fermenting yeast *Candida shehatae*. *Appl Microbiol Biotechnol* 23, 491-495.

Maniatis, T., E. F. Fritsch and J. Sambrook (1982) *Molecular cloning. A laboratory manual.* New York: Cold Spring Harbor Pitkanen J P, Rintala E, Aristidou A, Ruohonen L, Penttila M. (2005) Xylose chemostat isolates of *Saccharomyces cerevisiae* show altered metabolite and enzyme levels compared with xylose, glucose, and ethanol metabolism of the original strain. *Appl Microbiol Biotechnol.* 67(6):827-37.

Richard, P., Putkonen, M., Vaananen, R., Londesborough, J. and Penttila, M. (2002) The missing link in the fungal L-arabinose catabolic pathway, identification of the L-xylulose reductase gene. *Biochemistry* 41(20), 6432-7.

Verduyn, C., Postma, E., Scheffers, W. A. and Van Dijken, J. P. (1992) Effect of benzoic acid on metabolic fluxes in yeasts: a continuous-culture study on the regulation of respiration and alcoholic fermentation. *Yeast* 8(7), 501-17.

Weierstall, T., Hollenbuerg, C. P., and Boles, E. (1999) Cloning and characterization of three genes (SUT1-3) encoding glucose transporters of the yeast *Pichia stipitis*. *Mol Microbial* 31(3), 871-83.

Wieczorke, R., Krampe, S., Weierstall, T., Freidel, K., Hollenberg, C. P. and Boles, E. (1999) Concurrent knock-out of at least 20 transporter genes is required to block uptake of hexoses in *Saccharaomyces cerevisiae*. *FEBS Lett* 464 (3), 123-8.

Wiedemann, B. (2005) Molekulargenetische und physiologische Charakterisierung eines rekombinanten Pentosevergärenden Hefestammes. Diplomarbeit. Johann Wolfgang Goethe-Universität, Frankfurt am Main.

Wirth, R. (1993) Elektroporation: Eine alternative Methode zur Transformation von Bakterien mit Plasmid-DNA. *Forum Mikrobiologie* 11(507-515).

Zaldivar, J., Nielsen, J. and Olsson, L. (2001) Fuel ethanol production from lignocellulose: a challenge for metabolic engineering and process integration. *Appl Microbiol Biotechnol* 56(1-2), 17-34.

Zimmermann, F. K. (1975) Procedures used in the induction of mitotic recombination and mutation in the yeast *Saccharomyces cerevisiae*. *Mutat Res* 31(2), 71-86.

The invention claimed is:

1. An isolated nucleic acid molecule, encoding a polypeptide selected from the group consisting of:
   a) a polypeptide which is at least 95% identical to the amino acid sequence according to SEQ ID NO: 1 and has in vitro and/ or in vivo pentose transport function,
   b) a polypeptide which is identical to the amino acid sequence according to SEQ ID NO: 1 and has in vitro and/or in vivo pentose transport function, and
   c) a fragment of the polypeptide of a) or b) comprising the first 502 amino acids of SEQ ID NO: 1

2. The nucleic acid molecule according to claim 1, wherein the nucleic acid is at least 95% identical to the nucleic acid sequence according to SEQ ID NO: 2 or 3.

3. The nucleic acid molecule according to claim 1, further comprising a nucleic acid sequence which encodes a heterologous polypeptide.

4. The nucleic acid molecule according to claim 1, wherein the nucleic acid molecule comprises dsDNA, ssDNA, PNA, CNA, RNA or mRNA or combinations thereof.

5. A host cell, which comprises a nucleic acid molecule according to claim 1.

6. The host cell according to claim 5, which is a yeast cell.

7. The host cell according to claim 5, further comprising a nucleic acid molecule which encodes a protein of the arabinose metabolic pathway.

8. The host cell according to claim 7, wherein the nucleic acid molecule encodes a protein of the bacterial arabinose metabolic pathway.

9. A host cell of the strain MKY06-4P, which was deposited on Aug. 23, 2006 at the German Collection of Microorganisms and Cell Cultures under accession number DSM 18544.

10. A method for the production of a polypeptide, comprising cultivating a host cell containing a nucleic acid molecule that encodes the polypeptide under conditions by which said nucleic acid molecule is expressed wherein the polypeptide is selected from the group consisting of:
    a) a polypeptide which is at least 95% identical to the amino acid sequence according to SEQ ID NO: 1 and has in vitro and/ or in vivo pentose transport function,
    b) a polypeptide which is identical to the amino acid sequence according to SEQ ID NO: 1 and has in vitro and/or in vivo pentose transport function, and
    c) a fragment of the polypeptide of a) or b), comprising the first 502 amino acids of SEQ ID NO: 1.

11. The nucleic acid, according to claim 1, encoding a protein that is at least 99% identical to SEQ ID NO:1.

12. The nucleic acid, according to claim 2, wherein the nucleic acid is at least 99% identical to the nucleic acid sequence according to SEQ ID NO:2 or 3.

* * * * *

UNITED STATES PATENT AND TRADEMARK OFFICE
CERTIFICATE OF CORRECTION

PATENT NO.        : 8,063,194 B2
APPLICATION NO.   : 12/520487
DATED             : November 22, 2011
INVENTOR(S)       : Eckhard Boles and Marco Keller Page 1 of 1

It is certified that error appears in the above-identified patent and that said Letters Patent is hereby corrected as shown below:

IN THE SPECIFICATIONS:

Column 2
Line 63, "as arabinose" should read --as L-arabinose--

Column 4
Line 22, "*E. coli* araB" should read --*E. coli* araD--

Column 8
Line 34, "(+)pHL125 was" should read --(+) pHL125$^{re}$ was--

Column 9
Line 36, "his3-MAL2-8c" should read --his3-1 MAL2-8c--
Line 42, "h is 3-1" should read --his3-1--
Line 53, "p4251-17araD$^{re}$" should read --p425H7araD$^{re}$ --

Column 12
Line 7, "100 µmol" should read --100 pmol--

Column 13
Lines 19 and 20, "for arabinose" should read --for L-arabinose--

Column 16
Line 28, "(ORE)" should read --(ORF)--

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

PATENT NO. : 8,063,194 B2
APPLICATION NO. : 12/520487
DATED : November 22, 2011
INVENTOR(S) : Eckhard Boles and Marco Keller It is certified that error appears in the above-identified patent and that said Letters Patent is hereby corrected as shown below:

On the Title Page, Item (73) Assignee:

"Johann Wolfgang Goethe-Universität Frankfurt am Main, Frankfurt Am Main (DE)" should read --Butalco GmbH, Hunenberg (CH)--

Signed and Sealed this
Sixth Day of March, 2012

David J. Kappos
*Director of the United States Patent and Trademark Office*